United States Patent
Hossainy et al.

(10) Patent No.: US 10,064,745 B2
(45) Date of Patent: Sep. 4, 2018

(54) TAPERED SCAFFOLDS

(71) Applicant: Abbott Cardiovascular Systems Inc., Santa Clara, CA (US)

(72) Inventors: Syed Hossainy, Hayward, CA (US); Jason Van Sciver, Los Gatos, CA (US); Chad Abunassar, San Francisco, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 222 days.

(21) Appl. No.: 14/662,171

(22) Filed: Mar. 18, 2015

(65) Prior Publication Data

US 2015/0265438 A1 Sep. 24, 2015

Related U.S. Application Data

(60) Provisional application No. 61/955,127, filed on Mar. 18, 2014.

(51) Int. Cl.
| | | |
|---|---|---|
| *A61F 2/89* | (2013.01) | |
| *A61F 2/844* | (2013.01) | |
| *A61L 31/04* | (2006.01) | |
| *A61F 2/915* | (2013.01) | |
| *A61F 2/958* | (2013.01) | |
| *A61F 2/07* | (2013.01) | |

(52) U.S. Cl.
CPC ............. *A61F 2/89* (2013.01); *A61F 2/844* (2013.01); *A61F 2/915* (2013.01); *A61L 31/041* (2013.01); *A61F 2/958* (2013.01); *A61F 2002/072* (2013.01); *A61F 2002/91566* (2013.01); *A61F 2210/0004* (2013.01); *A61F 2230/0067* (2013.01); *A61F 2230/0078* (2013.01); *A61F 2250/0018* (2013.01); *A61F 2250/0023* (2013.01); *A61F 2250/0036* (2013.01); *A61F 2250/0039* (2013.01); *A61F 2250/0067* (2013.01)

(58) Field of Classification Search
CPC ..... A61F 2/82; A61F 2/86; A61F 2/89–2/915; A61F 2002/821; A61F 2002/825–2002/828; A61F 2002/91508–2002/91591
See application file for complete search history.

(56) References Cited

U.S. PATENT DOCUMENTS

| | | | | |
|---|---|---|---|---|
| 5,769,884 A * | 6/1998 | Solovay | ............... | A61F 2/07 606/194 |
| 5,868,780 A * | 2/1999 | Lashinski | ............ | A61F 2/90 606/191 |
| 5,876,432 A * | 3/1999 | Lau | ..................... | A61F 2/88 606/191 |

(Continued)

*Primary Examiner* — Darwin Erezo
*Assistant Examiner* — Jonathan Hollm
(74) *Attorney, Agent, or Firm* — Squire Patton Boggs (US) LLP

(57) ABSTRACT

A stent or scaffold has a tapered end or ends. The scaffold is made using an additive manufacturing technique such as stereolithography (SLA). The scaffold may take the shape of a frustum, or a scaffold having one or both of its ends flared. The scaffold has varying mechanical properties over its length, such as a varying ring stiffness, porosity or elasticity modulus. In one embodiment the strut and link widths change linearly from the distal to proximal ends.

7 Claims, 9 Drawing Sheets

(56) References Cited

U.S. PATENT DOCUMENTS

| | | | | |
|---|---|---|---|---|
| 6,200,335 B1 * | 3/2001 | Igaki | ............... | A61F 2/82 |
| | | | | 623/1.15 |
| 6,206,910 B1 | 3/2001 | Berry et al. | | |
| 7,740,791 B2 | 6/2010 | Kleine et al. | | |
| 2004/0230293 A1 * | 11/2004 | Yip | ............... | A61F 2/915 |
| | | | | 623/1.16 |
| 2004/0243216 A1 * | 12/2004 | Gregorich | ............... | A61F 2/91 |
| | | | | 623/1.15 |
| 2004/0267350 A1 * | 12/2004 | Roubin | ............... | A61F 2/91 |
| | | | | 623/1.13 |
| 2005/0215874 A1 * | 9/2005 | Wang | ............... | A61M 25/0108 |
| | | | | 600/407 |
| 2006/0229695 A1 * | 10/2006 | Brown | ............... | A61F 2/91 |
| | | | | 623/1.3 |
| 2006/0275340 A1 * | 12/2006 | Udipi | ............... | A61F 2/91 |
| | | | | 424/426 |
| 2008/0227056 A1 | 9/2008 | Bulard | | |
| 2010/0042202 A1 * | 2/2010 | Ramzipoor | ............... | A61F 2/91 |
| | | | | 623/1.15 |
| 2012/0271396 A1 * | 10/2012 | Zheng | ............... | A61L 27/58 |
| | | | | 623/1.2 |
| 2013/0085563 A1 * | 4/2013 | Stankus | ............... | A61L 31/041 |
| | | | | 623/1.15 |
| 2013/0261736 A1 * | 10/2013 | Kleiner | ............... | B29C 47/06 |
| | | | | 623/1.38 |
| 2015/0119908 A1 | 4/2015 | Consigny et al. | | |

* cited by examiner

TAPERED SCAFFOLDS

PRIORITY STATEMENT

This application claims priority to U.S. Provisional Application No. 61/955,127 filed Mar. 18, 2014, the entire contents of which are hereby incorporated by reference.

BACKGROUND OF THE INVENTION

Field of the Invention

This invention relates to additive manufacturing methods applied to bioresorbable implantable medical devices.

Description of the State of the Art

This invention relates generally to medical devices and methods of manufacturing medical device that are in whole or in part biodegradable. In particular, the devices include implantable medical devices for treating bodily lumens such as blood vessels. The devices include radially expandable endoprostheses that are adapted to be implanted in a bodily lumen. The devices also include devices that are generally adapted to delivery of drugs of an arbitrary shape such as particles.

An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a section or segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of a scaffold or scaffolding that includes a pattern or network of interconnecting structural elements or struts, formed from wires, tubes, or sheets of material rolled into a cylindrical shape. This scaffold gets its name because it physically holds open and, if desired, expands the wall of a passageway in a patient. Typically, stents are capable of being compressed or crimped onto a catheter from a fabricated diameter to a reduced diameter so that they can be delivered to and deployed at a treatment site.

Delivery includes inserting the stent through small lumens using a catheter and transporting it to the treatment site. Deployment includes expanding the stent to a larger target diameter once it is at the desired location. During deployment the stent makes contact with the vessel wall as it expands and expands the vessel to the larger target diameter. Mechanical intervention with stents has reduced the rate of restenosis as compared to balloon angioplasty.

Stents are used not only for mechanical intervention but also as vehicles for providing biological therapy. Biological therapy uses medicated stents to locally administer a therapeutic substance to a blood vessel. The therapeutic substance can also mitigate an adverse biological response to the presence of the stent. For example, the stent can deliver an antiproliferative agent to the vessel to prevent or mitigate neointimal proliferation caused by the stent implantation which could result in narrowing of the vessel at the site of the stent implantation. Additionally or alternatively, an anti-inflammatory agent can be delivered to reduce inflammation to the vessel wall due to the stent implantation.

A medicated stent may be fabricated by coating the surface of either a metallic or polymeric scaffolding with a polymeric carrier that includes an active or bioactive agent or drug. Polymeric scaffolding may also serve as a carrier of an active agent or drug.

The stent must be able to satisfy a number of mechanical requirements. The stent must have sufficient radial strength so that it is capable of withstanding the structural loads, namely radial compressive forces imposed on the stent as it supports the walls of a vessel at the expanded target diameter. Radial strength, which is the ability of a stent to resist radial compressive forces, relates to a stent's radial yield strength and radial stiffness around a circumferential direction of the stent. A stent's "radial yield strength" or "radial strength" (for purposes of this application) may be understood as the compressive loading, which if exceeded, creates a yield stress condition resulting in the stent diameter not returning to its unloaded diameter, i.e., there is irrecoverable deformation of the stent. When the radial yield strength is exceeded the stent is expected to yield more severely and only a minimal force is required to cause major deformation.

Once expanded, the stent must adequately provide lumen support during a time required for treatment in spite of the various forces that may come to bear on it, including the cyclic loading induced by the beating heart. In addition, the stent must possess sufficient flexibility with a certain resistance to fracture.

Stents made from biostable or non-erodible materials, such as metals, have become the standard of care for percutaneous coronary intervention (PCI) as well as in peripheral applications, such as the superficial femoral artery (SFA). Such stents have been shown to be capable of preventing early and later recoil and restenosis. These permanent stents include bare metal stents and drug eluting stents which include a metallic base or scaffold with a polymer and drug coating.

In order not to affect healing of a diseased blood vessel, the presence of the stent is necessary only for a limited period of time. There are certain disadvantages to the presence of a permanent implant in a vessel such as compliance mismatch between the stent and vessel and risk of embolic events such as late stent thrombosis. To alleviate such disadvantages, a stent can be made from materials that erode or disintegrate through exposure to conditions within the body. Thus, erodible portions of the stent can disappear from the implant region after the treatment is completed, leaving a healed vessel. Stents fabricated from biodegradable, bioabsorbable, bioresorbable, and/or bioerodable materials such as bioabsorbable polymers can be designed to completely erode only after the clinical need for them has ended.

A compliance-matching stent structure exhibits a high degree of radial flexibility at the end rings of the stent. These relatively 'high compliance' end-ring structures allow the deployed stent to better match the compliance of the adjacent vessel wall, thereby providing for improved pulsatile hemodynamics. In order to also provide sufficient scaffolding support against compressed plaque, the stent structure is relatively stiff in the middle-section of the stent. An example of a compliance-matching stent is described in U.S. Pat. No. 6,206,910. While the structure described in this publication aims to utilize low end-ring radial stiffness to enable improved hemodynamics, it may not adequately scaffold plaques acutely, which is often the primary function of a deployed stent. Calcified lesions, ostial lesions, and total occlusions all require a high degree of radial stiffness to avoid localized collapse after deployment. Against these challenges and others, the structure disclosed in U.S. Pat. No. 6,206,910, may not perform adequately. For example, when stenting a lesion with even a modest plaque volume, longitudinal plaque migration is known to occur. In these cases the stent should have acute radial stiffness sufficient at the ends of the deployed structure during an acute period, i.e., within the first 1-2 weeks, or month following implantation. At later timeframes after deployment, however, a stented vessel will remodel positively over time, thereby requiring less radial stiffness. For this reason, a stent structure is desired that provides high end-ring radial stiffness acutely, and low end-ring radial stiffness in the long term after vascular remodeling occurs.

The geometrical structure, composition, and geometrical distribution of components of a device are limited by conventional fabrication techniques that rely on "subtractive" fabrication methods. The treatment of various bodily disorders may be immensely improved by devices that have geometrical structure, composition, and geometrical distribution of components that are difficult or impossible to attain with conventional subtractive fabrication techniques.

SUMMARY OF THE INVENTION

According to one aspect, an implant site is a tapered segment of a blood vessel and a scaffold comprises a tapered shape in conformity to the tapered segment. In a preferred embodiment the scaffold resembles a frustum, or at least one end portion of the scaffold is tapered or has a frusto-conical shape. The scaffold may be made from both a bioresorable material and a durable polymer. Additive manufacturing processes such as stereo lithography may be used to make a bioresorbable scaffold according to the embodiments. Fused deposition methods may be used to make a durable scaffold (or stent) according to the embodiments. In some embodiments the scaffold (or stent) is configured for being crimped to a balloon and delivered to a vessel site on a balloon catheter. In other embodiments the stent (or durable scaffold) is configured for serving as a soft-tissue implant.

Additive Manufacturing (AM) is a preferred method of manufacture for embodiments of the invention. For example, with respect to the frustum illustrated in FIG. 2, AM offers two advantages:

(1) The prescribed taper precludes a subtractive method such as extrusion followed by laser machining. Extrusion is preferred for constant cross-section scaffolds or stents. Laser machining is also preferred for removing material from a constant cross-section tube due to the challenges with maintaining a precision focal point for the laser if the tubing is not rotated concentrically in the cutting plane. The scaffolds described here are not constant cross-section. The scaffolds disclosed are tapered.

(2) Maintaining a constant aspect ratio of the strut cross-section is preferred to ensure the crimping behavior of the scaffold is consistent along the length. Therefore, if a strut width is changing to maintain an optimal material-to-artery ratio along the length, then so too does the wall thickness. Crowns of the scaffold may distort out of plane if a proper aspect ratio is not maintained during crimping. Subtractive methods of manufacturing do not allow for this type of controlled aspect ratio, e.g., changing the scaffold wall thickness as the strut width changes; however AM is very capable of achieving precise control over these relationships. The preferred AM technology used to manufacturing the tapered scaffold is SLA. The precise geometry specified for the scaffold requires X, Y & Z coordinate accuracy in the range of 1-10 µm. This level of control can only be achieved by SLA.

Scaffolds disclosed described herein may be used to address clinical needs in a number of areas including, but not limited to, coronary vascular disease, peripheral vascular disease, local oncology therapy, AV fistula implant, neurodegenerative disease, congestive heart failure, aneurysm, eliminating amputation, congenital heart disease, and plugging holes in arteries. In particular, scaffolds according to the disclosure are intended for being implanted in the following specific anatomies or serving the following specific functions:

According to a first embodiment of a scaffold, e.g., TABLE A, a tapered scaffold may be applied to long vascular lesions, such as supra femoral artery (FSA) disease. The scaffold length in these applications can be greater than 100 mm. The scaffold may also be applied to Infrapopliteal lesions.

According to second and third embodiments, an arteriovenous graft (AVG) may be used with dialysis access patients and to treat an Abdominal Aortic Aneurysm (AAA). The second and third embodiments in general apply to soft tissue implants that require matching mechanical compliance at the ends of the implant.

In accordance with the foregoing disclosure and included within the scope of the invention, there is a medical device including a tapered or frustum scaffold/stent, a delivery system comprising the medical device including a balloon catheter, and method for making and/or assembling such a medical device having one or more, or any combination of the following things (1)-(22):

(1) The scaffold 40, 60 may have two, three or four links 48 connecting adjacent rings at respective Y and W crowns. The number of crowns per ring may be 6, 7, 8, 9 or between 8 and 12.

(2) An aspect ratio (AR) of width to thickness (w/t) for a link is between about 0.5 and 1.5, between about 1.0 and 1.5, or between about 0.4 and 0.9.

(3) An AR that is substantially constant for all of the struts of the rings of a tapered scaffold.

(4) An aspect ratio (AR) of width to thickness (w/t) for a strut is between 0.5 and 1.5, between 1.0 and 1.5, or between 0.5 and 0.9.

(5) A change in the diameter of a ring over the length of a tapered scaffold according to EQ. 1A or 2A.

(6) A change in the width of a ring strut over the length of a tapered scaffold according to EQ. 1B or 2B.

(7) A tapered scaffold crimped to a balloon of a balloon catheter by a crimping process.

(8) Any combination of diameters or diameter ranges, strut widths or range of strut widths, or tangents of a taper angle for a strut or diameter of a frustum scaffold intended for the respective right coronary artery (e.g., distal or proximal right coronary artery), left anterior descending artery (e.g., distal or proximal right coronary artery), or left circumflex artery (e.g., distal or proximal right coronary artery) as provided in TABLE 2.

(9) A method for treating a lesion site located in any of the Right Coronary Artery, Left Anterior Descending Artery and Left Circumflex Artery, including providing a crimped tapered scaffold (e.g., frustum) on a balloon catheter and deploying the tapered scaffold at the lesion site.

(10) A tapered scaffold intended for the Right Coronary Artery, Left Anterior Descending Artery, Left Circumflex Artery, or superficial femoral artery.
(11) A frangible link made with 85:15 PGA:PLLA w/w ratio and strut width will be made 100 μm and thickness 25 μm. Or 75:25 PEG:PGA w/w ratio can be used for a same strut dimension.
(12) A tapered scaffold having compliance matched ends.
(13) A tapered scaffold covered by a sheath, wherein the sheath has a first surface porosity at a proximal end and at a distal end, and a second surface porosity between the ends, and the first surface porosity is greater than the second surface porosity.
(14) A graft comprising a tapered scaffold intended for an anastomosis, wherein the graft has ends configured to have a compliance to match a compliance of an artery and/or vein being connected, joined or replaced by the graft.
(15) A tapered scaffold having all, or any one of the material or mechanical properties disclosed in TABLE A.
(16) A tapered scaffold having all, or any one of, or any combination of the material or mechanical properties disclosed in TABLE B.
(17) A tapered scaffold having all, or any one of, or any combination of the material or mechanical properties disclosed in TABLE C, in any combination.
(18) A tapered scaffold having all, or any one of, or any combination of the material or mechanical properties disclosed in TABLE 1, in any combination.
(19) A medical device, comprising: frustum scaffold made from a polymer, the frustum comprising: a network of rings interconnected by links, wherein a ring is formed by struts connected at crowns to form a zig-zag or undulating pattern of struts about a bore axis of the frustum, and wherein a link connects a ring to an adjacent ring at either a Y crown or a W crown.
(20) The medical device according to (19), in combination with one or more of, or any combination of the following things (a) through (l):
  (a) wherein struts of rings have a width, and wherein the struts of rings linearly vary from a distal end to a proximal end of the frustum;
  (b) wherein a proximal end of the scaffold has a smaller diameter than a distal end of the frustum, and wherein a width of a strut at a medial portion between the distal and proximal ends is greater width than a width of a strut at the proximal end, and a width of a strut at the distal end is greater than the width of the strut at the medial portion;
  (c) wherein links have a width, and wherein the struts of rings linearly vary from a distal end to a proximal end of the frustum;
  (d) wherein the frustum has a linear taper;
  (e) wherein the frustum is encased in a sheath;
  (f) wherein the sheath has a higher porosity at the distal and/or proximal than at a middle portion thereof;
  (g) wherein the diameter at a proximal end is between 2 to 5 mm, a diameter at a distal end is between 3 to 8 mm and a length of the frustum is between 100 mm and 150 mm;
  (h) wherein a strut width for rings of the frustum ranges between about 50 microns and 150 microns and a strut width for a ring medial of a distal end ring and a proximal end ring of the frustum is defined by EQ. 1B;
  (i) a catheter comprising the medical device crimped to a balloon of the catheter;
  (j) wherein an elasticity modulus at a first end is constant and has a value range of about 0.5 to 1.5 GPa, 0.5 to 0.99 GPa or 1.1 to 1.5 GPa, at a second end the elasticity modulus is constant and has a value range of about 0.5 to 1.5 GPa and linearly varies at a middle section between the ends and has an elasticity modulus of 1.6 to 3.5 GPa, 1.0 to 3.5 GPa or 1.05 to 1.5 GPa;
  (k) wherein at a proximal or distal end a scaffold material is PLLA-co-PCL blended with PEO or PVP, and in a middle portion a scaffold material is PLLA-co-PCL; and/or
  (l) wherein an aqueous swellability at a first end is constant and has a value range of 5-20% w/w, at a second end is constant at a value range of 5-20% w/w; and is constant for middle portion between the flared ends with a range of 0.05%-2.5%.
(21) A medical device, comprising: a scaffold made from a polymer and having a tapered or flared end, the frustum comprising: a network of rings interconnected by links, wherein a ring is formed by struts connected at crowns to form a zig-zag or undulating pattern of struts about a bore axis of the frustum, and wherein a link connects a ring to an adjacent ring at either a Y crown or a W crown.
(22) The medical device according to (21), in combination with one or more of, or any combination of the following things (a) through (l):
  (a) wherein struts of rings have a width, and wherein the struts of rings linearly vary from a distal end to a middle portion of the scaffold;
  (b) wherein struts of rings have a width, and wherein the struts of rings linearly vary from a proximal end to the middle portion of the scaffold, and wherein rings of the middle portion each have about the same diameter;
  (c) wherein links have a width, and wherein the struts of rings linearly vary from a distal end to a middle portion of the scaffold;
  (d) wherein the scaffold has a linear taper at one or both ends;
  (e) wherein the scaffold is encased in a sheath;
  (f) wherein the sheath has a higher porosity at the distal and/or proximal end than at a middle portion thereof;
  (g) wherein the diameter at a proximal end is between 2 to 5 mm, a diameter at a distal end is between 3 to 8 mm and a length of the tapered scaffold is between 100 mm and 150 mm;
  (h) wherein a strut width for rings of the tapered scaffold ranges between about 50 microns and 150 microns and a strut width for a ring medial of a distal end ring and a proximal end ring of the frustum is defined by EQ. 2B;
  (i) a catheter comprising the medical device crimped to a balloon of the catheter;
  (j) wherein an elasticity modulus at a first flared end is constant and has a value range of about 0.5 to 1.5 GPa, 0.5 to 0.99 GPa or 1.1 to 1.5 GPa, at a second flared end the elasticity modulus is constant and has a value range of about 0.5 to 1.5 GPa and linearly varies at a middle section between the flared ends and has an elasticity modulus of 1.6 to 3.5 GPa, 1.0 to 3.5 GPa or 1.05 to 1.5 GPa;

(k) wherein at the flared end a scaffold material is PLLA-co-PCL blended with PEO or PVP, and in a middle portion a scaffold material is PLLA-co-PCL; and/or (l) wherein an aqueous swellability at a first flared end is constant and has a value range of 5-20% w/w, at a second flared end is constant at a value range of 5-20% w/w; and is constant for middle portion between the flared ends with a range of 0.05%-2.5%.

INCORPORATION BY REFERENCE

Figure 1:
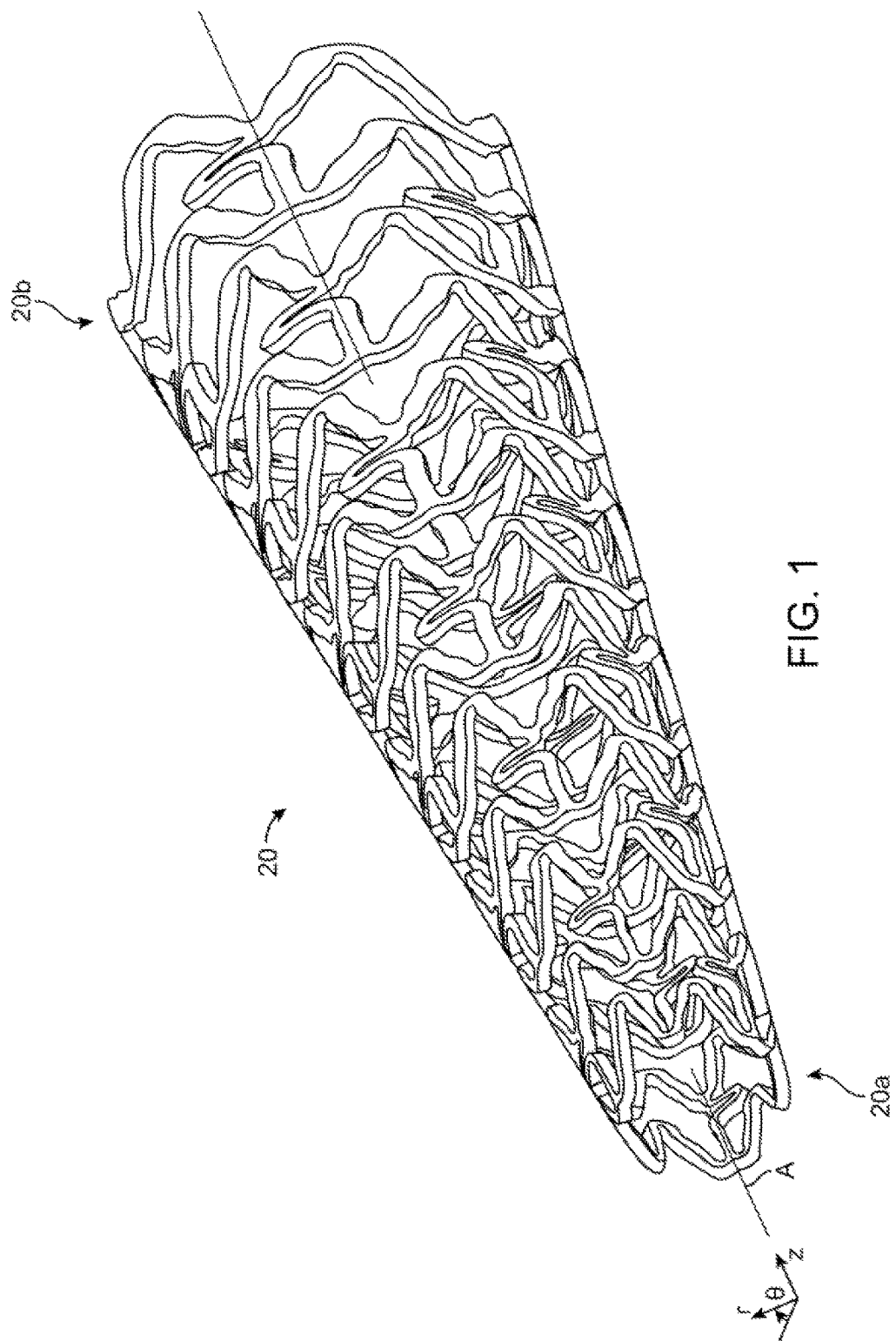
FIG. 1 depicts a perspective view of a frustum scaffold according to a first aspect of the disclosure.

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

DETAILED DESCRIPTION OF THE INVENTION

Embodiments of the present invention include manufacturing of bioresorbable implantable medical devices using additive manufacturing methods (AM) methods or techniques. The embodiments further include bioresorbable implantable medical devices manufactured by AM methods having properties tailored or designed for particular treatments.

The terms "about" or "approximately" mean 30%, 20%, 15%, 10%, 5%, 4%, 3%, 2%, 1.5%, 1%, between 1-2%, 1-3%, 1-5%, or 0.5%-5% less or more than, less than, or more than a stated value, a range or each endpoint of a stated range, or a one-sigma, two-sigma, three-sigma variation from a stated mean or expected value (Gaussian distribution). For example, d1 about d2 means d1 is 30%, 20%, 15%, 10%, 5%, 4%, 3%, 2%, 1.5%, 1%, or between 1-2%, 1-3%, 1-5%, or 0.5%-5% different from d2. If d1 is a mean value, then d2 is about d1 means d2 is within a one-sigma, two-sigma, or three-sigma variation from d1.

It is understood that any numerical value, range, or either range endpoint (including, e.g., "approximately none", "about none", "about all", etc.) preceded by the word "about," "substantially" or "approximately" in this disclosure also describes or discloses the same numerical value, range, or either range endpoint not preceded by the word "about," "substantially" or "approximately."

A "crimping" or "inelastic crimping" of a stent or scaffold means, unless otherwise stated, a significant plastic or inelastic deformation of the stent or scaffold (body), such that when a radial restraint is removed from the crimped body, e.g., a constraining sheath is withdrawn, the scaffold or stent will change diameter (due to elastic recoil) by no more than about 5%, 10%, 20%, 30% or 50% increase from the crimped diameter. A body crimped to the balloon is held to the balloon by a retention force. A crimped body is deployed within the body by a balloon that imposes a significant inelastic or plastic deformation to expand the body to a deployed expanded or post-dilation diameter. The crimped body when deployed also has elastic recoil causing it to reduce in diameter by about 1, 2, 1-5%, 5-10% or 10%.

A "frustum" is a cone that remains after its upper part has been cut off by a plane parallel to its base, or that is intercepted between two such planes. For purposes of this disclosure, a "frustum scaffold" adopts this same meaning for frustum, with the exception that the disclosure also includes a scaffold that has both a linear and non-linear taper. By non-linear it is meant that the taper is curved, rather than straight. For instance, in cylindrical coordinates $(z, r, \theta)$ where the Z coordinate extends along the longitudinal or bore axis, r is the radial distance from the z axis and $\theta$ is the angle between a datum and the vector extending to radius r (see FIG. 1), the scaffold has a linear taper when $r=r(z)$ and a non-linear taper when $r=r(z^n)$ (n>1), meaning the change in radius is a linear function of z or z raised to the power n, respectively. Thus, a non-linear taper means a curved taper because r varies as a polynomial of z. A non-linear or non-constant taper is included within the meaning of a frustum scaffold. Frustum scaffolds according to the disclosure are also monotonically increasing or decreasing from proximal to distal ends (consistent with the meaning of "frustum').

Whenever the term "diameter" appears in the disclosure, it shall mean either outer diameter or inner diameter. Thus, when a "diameter" is given it shall be understood that either the inner diameter or the outer diameter is being disclosed. Moreover, when a diameter value is given for a ring, or at a section of a scaffold disclosed herein, the diameter is intended to mean an average diameter over the designated section (e.g., a ring diameter).

The terms width and thickness are intended to mean a maximum or minimum measured width or thickness over the designated section, or an average (mean or median) width or thickness over the measured section. Thus a width or thickness for a strut or link refers to the maximum, minimum or average (mean or median) over the length or extent of a strut or link. Both types of measurements are implied in the disclosure.

The terms bioresorbable, biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and absorption of the polymer can be caused by, for example, hydrolysis and metabolic processes.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is increased, the heat capacity increases. The increasing heat capacity corresponds to an increase in heat dissipation through movement. Tg of a given polymer can be dependent on the heating rate and can be influenced by the thermal history of the polymer as well as its degree of crystallinity. Furthermore, the chemical structure of the polymer heavily influences the glass transition by affecting mobility.

The Tg can be determined as the approximate midpoint of a temperature range over which the glass transition takes place. [ASTM D883-90]. The most frequently used definition of Tg uses the energy release on heating in differential scanning calorimetry (DSC). As used herein, the Tg refers to a glass transition temperature as measured by differential scanning calorimetry (DSC) at a 20° C./min heating rate.

The "melting temperature" (Tm) is the temperature at which a material changes from solid to liquid state. In polymers, Tm is the peak temperature at which a semicrystalline phase melts into an amorphous state. Such a melting process usually takes place within a relative narrow range (<20° C.), thus it is acceptable to report Tm as a single value.

"Molecular weight" (MW) may refer to number average molecular weight or weight average molecular weight. The molecular weight of the polymer in implants, scaffolds, nanoparticles may be 30 to 70 kDa, 70 to 100 kDa, 100 to 150 kDa, 150 to 200 kDa, 200 to 250 kDa, 250 to 300 kDa, or greater than 300 KDa.

FIG. 1 is a perspective view of a tapered scaffold that takes the shape of a frustum according to a first aspect of disclosure. The frustum 20 has a bore axis that is collinear with the z axis of the cylindrical coordinate system (r, θ, z) shown in FIG. 1. The frustum has a proximal end 20a and a distal end 20b. The structure is a scaffold made from a bioresorbable material and having a network of interconnected elements comprising rings 24 interconnected by links 28.

Figure 2:
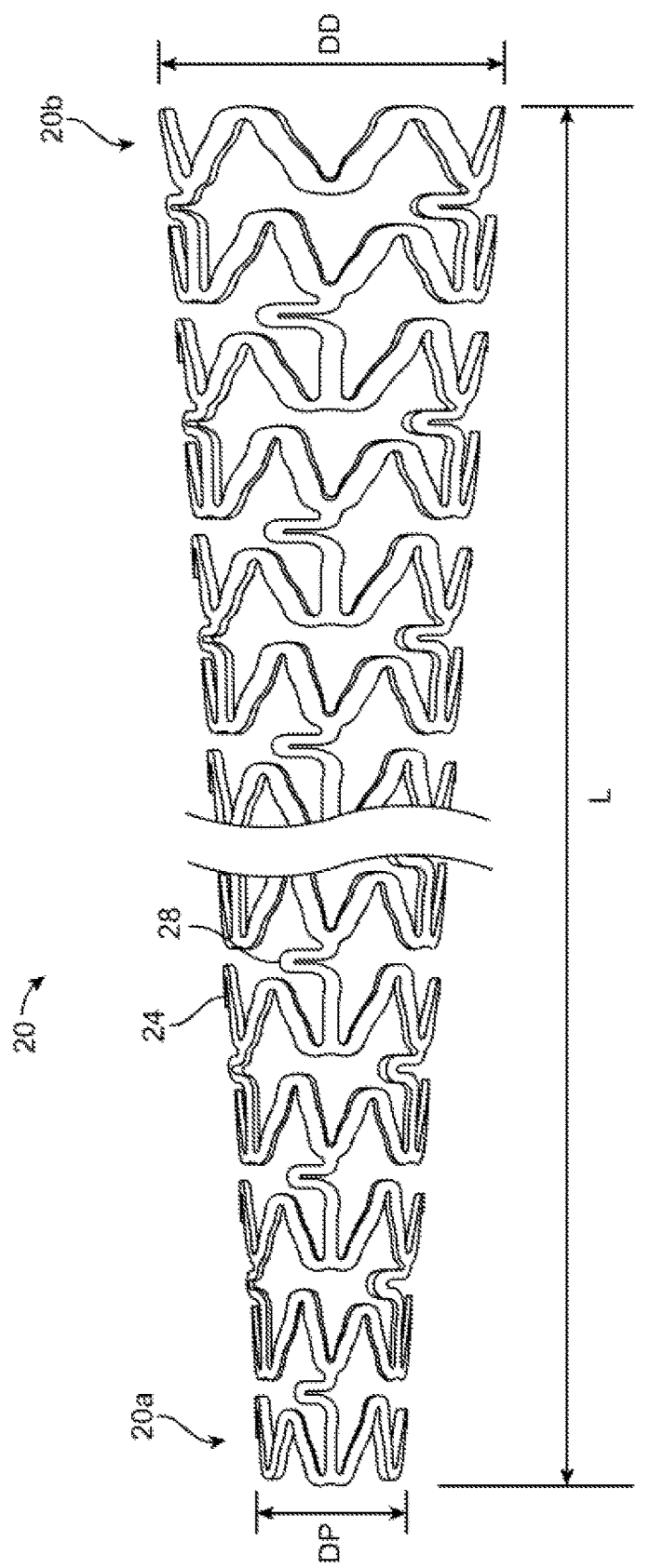
FIG. 2 is a side view of the frustum depicted in FIG. 1.

FIG. 2 illustrates a view of the frustum 20 in the r-z plane of FIG. 1. This embodiment of a frustum scaffold may be formed by an additive manufacturing process to produce the varying geometry and mechanical properties of the frustum, as explained in more detail below. The body 20 has a proximal end 20a and distal end 20b. The proximal end 20a has a diameter (DP) and the distal end has a second diameter (DD). DD is greater than DP, the taper for the body 20 is about linear and monotonically decreasing from the distal to proximal end for this embodiment. The taper for frustum 20 is (DD–DP)/L and the taper angle is the arctangent of (DD–DP)/L, where L is the distance from the proximal end 20a to distal end 20b. The network of rings 24 and links 28 is shown in greater detail in FIG. 3. Although the above definition of taper refers to a distal end diameter being greater than the proximal end, the terms "distal" and "proximal" should not be interpreted as meaning that the frustum scaffold necessarily has its larger diameter end at a more distal end of a delivery catheter. The frustum may be arranged on the catheter so that its proximal end has a larger or smaller diameter than its distal end.

Figure 3:
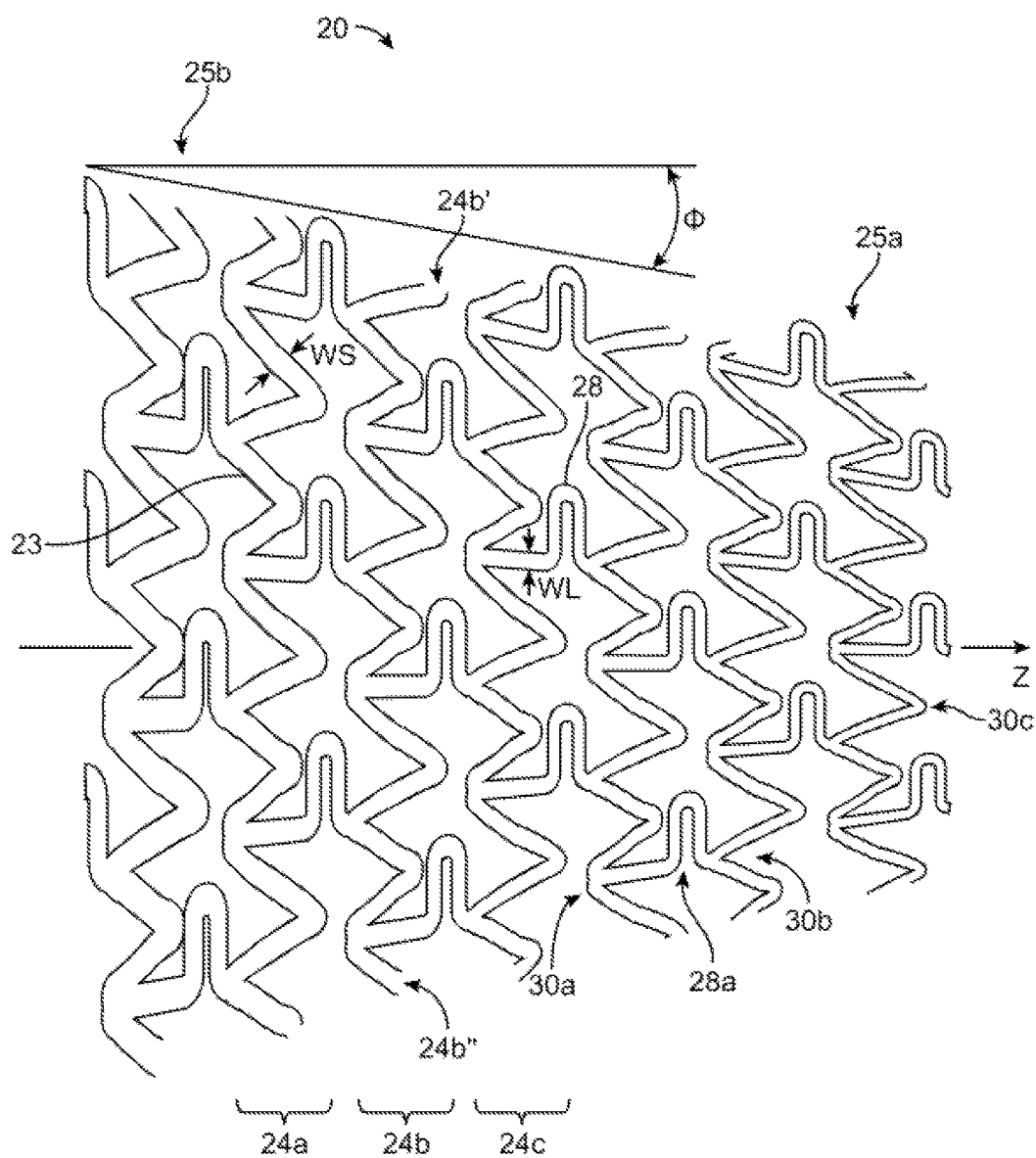
FIG. 3 is a planar view of the frustum of FIG. 1.
Figure 4A:
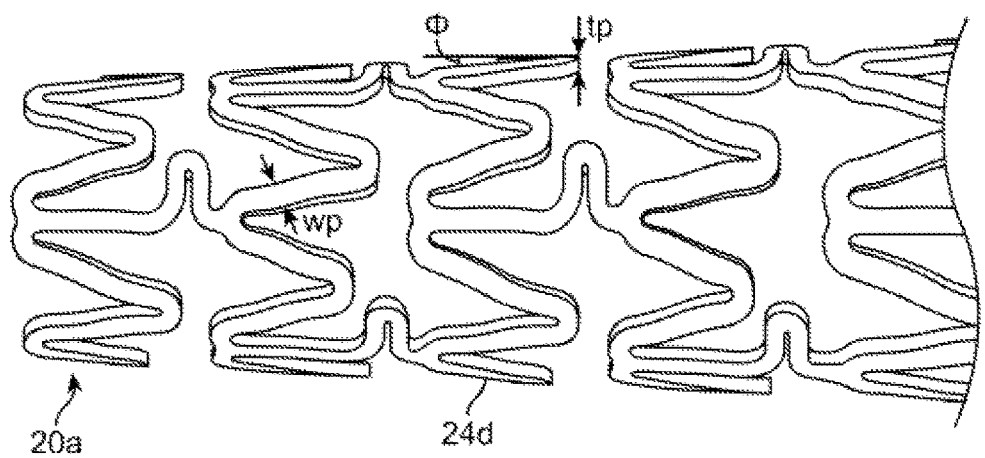
FIGS. 4A-4B are proximal and distal end portions, respectively, of the frustum of FIG. 2.
Figure 4B:
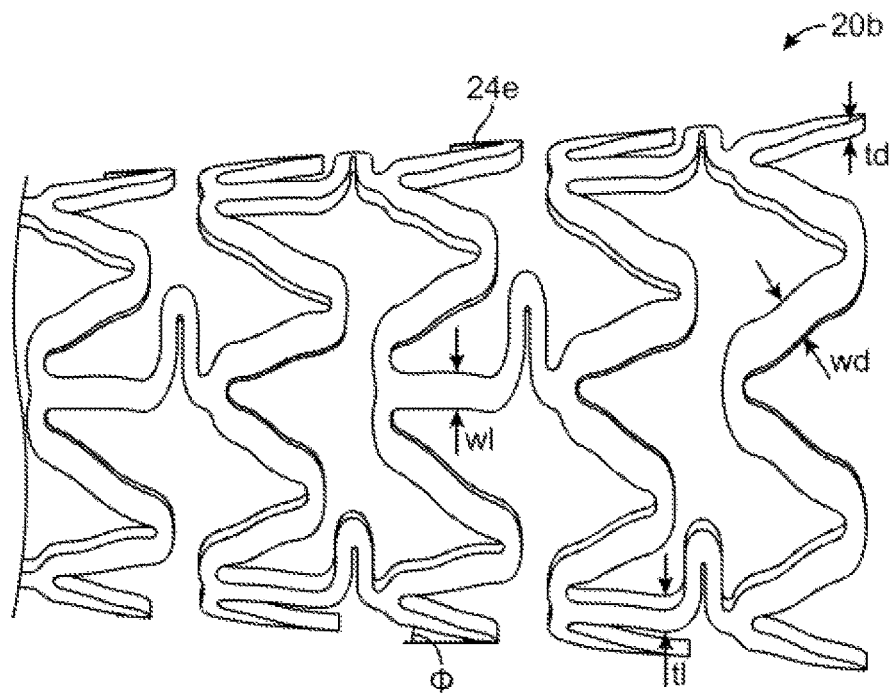

A mid-portion of the frustum 20 is shown in FIG. 3. This view may be understood as a view one would see if the frustum 20 where cut along its length, then unrolled and laid flat. Thus, the portions 24b' and 24b" of the ring 24 would correspond to the cut line, or the portions 24b' and 24b" refer to the same point on the ring 24 before the frustum is cut and laid flat. Shown is the taper angle φ and z axis from FIG. 1. A ring 24 includes struts 23 that are interconnected with each other at crowns 30a, 30b or 30c. A strut may have a rectangular cross-section characterized by an aspect ratio (AR), which is defined as the ratio of the width (ws) to the thickness (ts) or AR for a strut is ws divided by ts. Referring briefly to FIGS. 4A and 4B the thickness and width for struts of rings 24 located near the proximal and distal ends are wp, tp, wd, and td, respectively, as shown. A link may have a rectangular cross-section characterized by an aspect ratio (AR), which is defined as the ratio of the width (wl) over thickness (tl), or the AR for a link is wl divided by tl (see FIG. 4B).

Referring to FIGS. 3, 4A and 4B, a ring 24 may form a zig-zag or undulating pattern about the frustum's bore axis A and have a tilt or taper corresponding to about the taper angle φ of the frustum. This is indicated in FIGS. 4A and 4B. The struts forming ring 24d (FIG. 4A) near the proximal end 20a are arranged to give the ring's lengthwise extent (z axis dimension) a taper, which in this embodiment is φ. Similarly, struts forming ring 24e (FIG. 4B) near the distal end 20b are arranged to give the ring's lengthwise extent (z axis dimension) the taper φ. These tapers at proximal and distal ends may be the same or different. Moreover, the tapers may change from ring to ring. A frustum having this non-constant taper between one or more adjacent rings is considered a frustum having a non-linear taper. The ring 24 may alternatively have no tilt or taper, but instead have a slightly less, or greater outer diameter than its adjacent ring proximal or distal, respectively, so that over its length the scaffold also has the shape of a frustum according to the disclosure.

Struts 23 of a ring connect at either a U crown 30c, W crown 30a or Y crown 30b. A link 28a connects at one end to a Y crown 30b and at its opposite end to a W crown 30a. For the embodiment depicted in FIGS. 1-3 the frustum has three links 28 connecting adjacent rings. There are three links 28 that connect ring 24a to ring 24b and three different links that connect ring 24b to ring 24c. There is no link that connects to a U crown 30c.

The frustum 20 also has ring and link sizes that vary in dimension from proximal to distal end. In some embodiments the link and/or ring sizes vary in about the same proportion as the outer diameter changes from proximal to distal ends, although the disclosure contemplates other constructions as well in response to a clinical need. The embodiment illustrated in FIGS. 1-3, 4A and 4B has its struts 23 and link 28 widths, e.g., ws and wl, vary in proportion to the change in outer diameter along the z-axis. Thus, the widths wp (FIG. 4A) are substantially smaller than wd because the diameter at the proximal end is less than the diameter at the distal end.

According to some embodiments the outer diameter and width of a strut (or link) of the $i^{th}$ ring (or link) of the frustum of FIG. 2 may be found using EQS. 1A and 1B, respectively.

$$Di = ((DD - DP)/L) * zi + DP \qquad \text{EQ. 1A}$$
$$= \text{Tan}(\phi) * zi + DP$$

$$Wi = ((WD - WP)/L) * zi + WP \qquad \text{EQ. 1B}$$
$$= \text{Tan}(\phi) * zi + WP$$

wherein,
DP and DD are the diameters at the proximal and distal ends, respectively, L is the length of the scaffold, and WP and WD are widths of struts at the proximal and distal ends, respectively;
$zi$ is the distance in z from the proximal end to the mid-point of the ith ring (or midpoint of ith link connected to the ith ring on its distal side);
the taper angle φ may range from 5 and 15 degrees, more narrowly between 0.5 to 2 degrees 1 to 5 degrees, 4 to 6 degrees, 5-10 degrees, or more narrowly between 5-8 degrees (these ranges will be appreciated in view of the scope of contemplated clinical needs addressed by the invention); and $D0$ and $W0$ is the diameter and width, respectively, for the ring and strut (or link), respectively, for the first ring at the proximal end 20a.

For example, in one embodiment a frustum has a length of 150 mm (L), proximal end diameter 3.5 mm (DP), distal end diameter 5.5 mm (DD), 13 rings, a strut width at the first ring of 50 μm (WP) and a strut width at the $13^{th}$ ring of 100 (WD). The diameter and strut width at, for example, the $6^{th}$ ring located 70 mm from the proximal end is computed as follows.

To compute the $6^{th}$ ring diameter, D6, use EQ. 1A. First, the tangent of the diameter taper angle is $(DD-DP)/L=(5.5-3.5)/150=0.0133$. The diameter of the sixth ring is therefore $D6=(0.01333)*70+3.5=4.4$ mm.

To compute the $6^{th}$ ring width, W6, use EQ. 1B. First, the tangent of the width taper angle is $(WD-WP)/L=(0.1-0.05)/150=0.000333$. A strut width for the sixth ring is therefore $W6=(0.000333)*70+0.05=73$ μm.

Figure 5A:
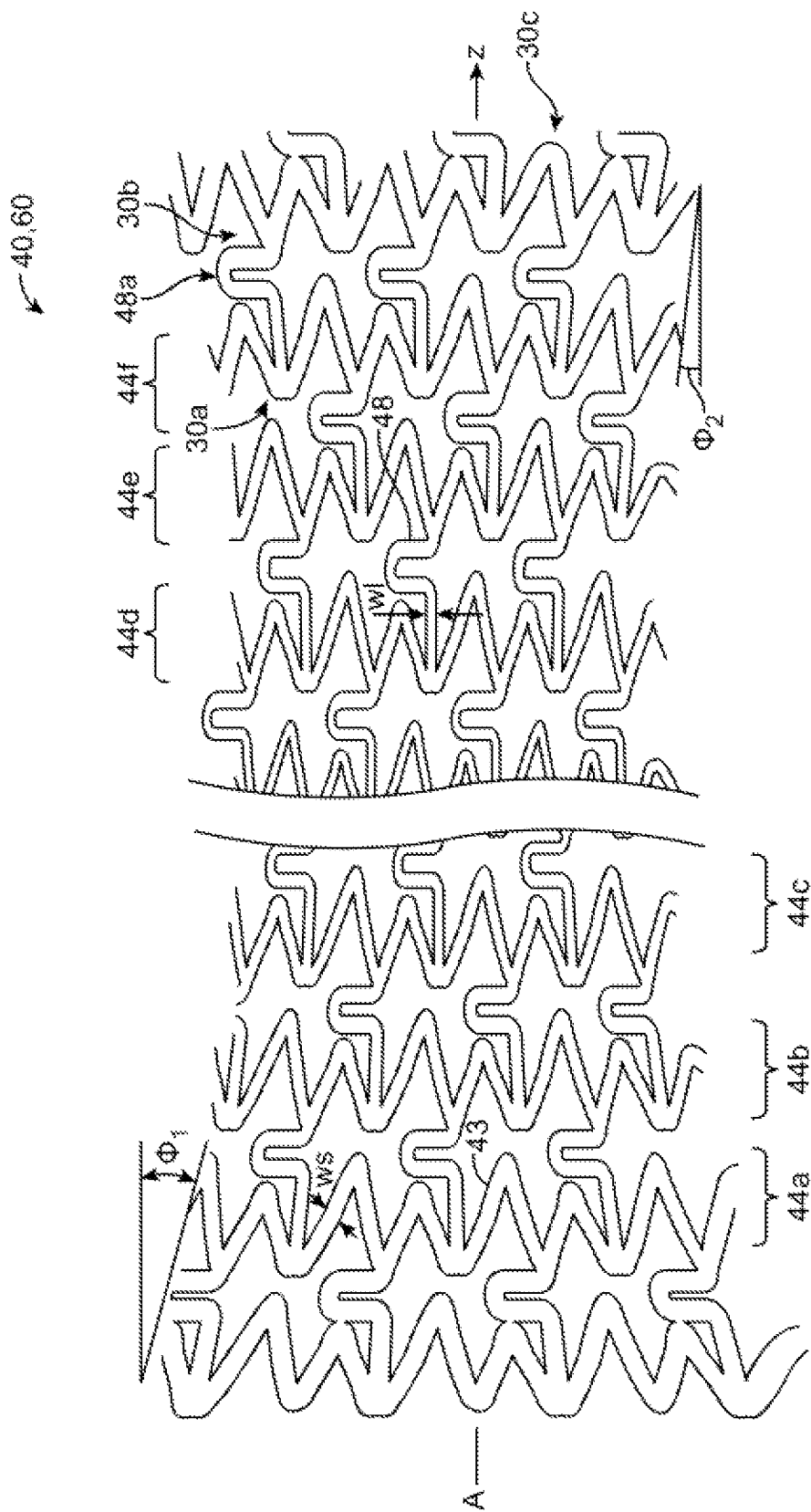
FIG. 5A is a planar view of a tapered scaffold according to a second aspect of the disclosure.
Figure 5B:
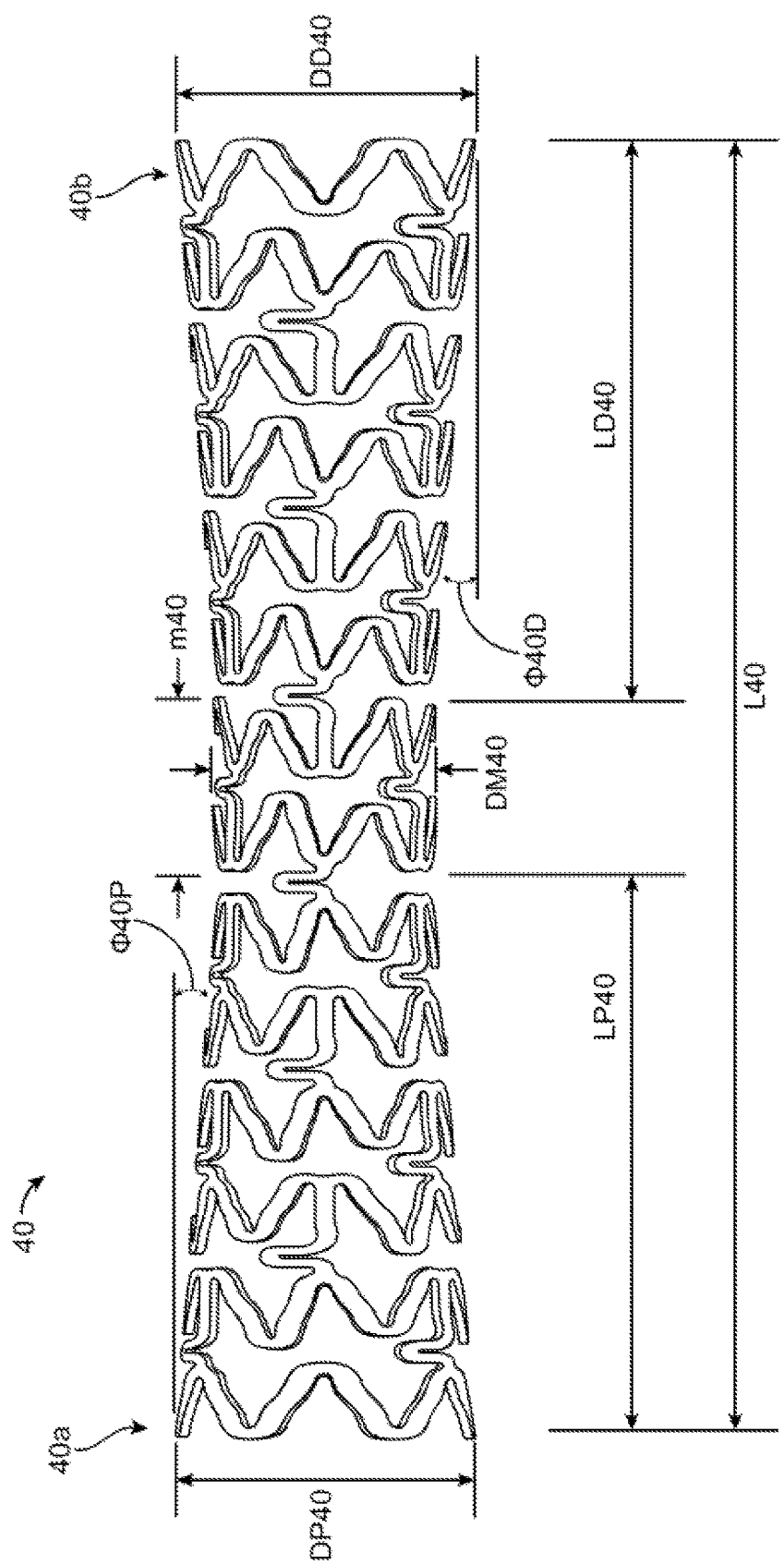
FIG. 5B is a side view of a tapered scaffold according to a third aspect of the disclosure.
Figure 5C:
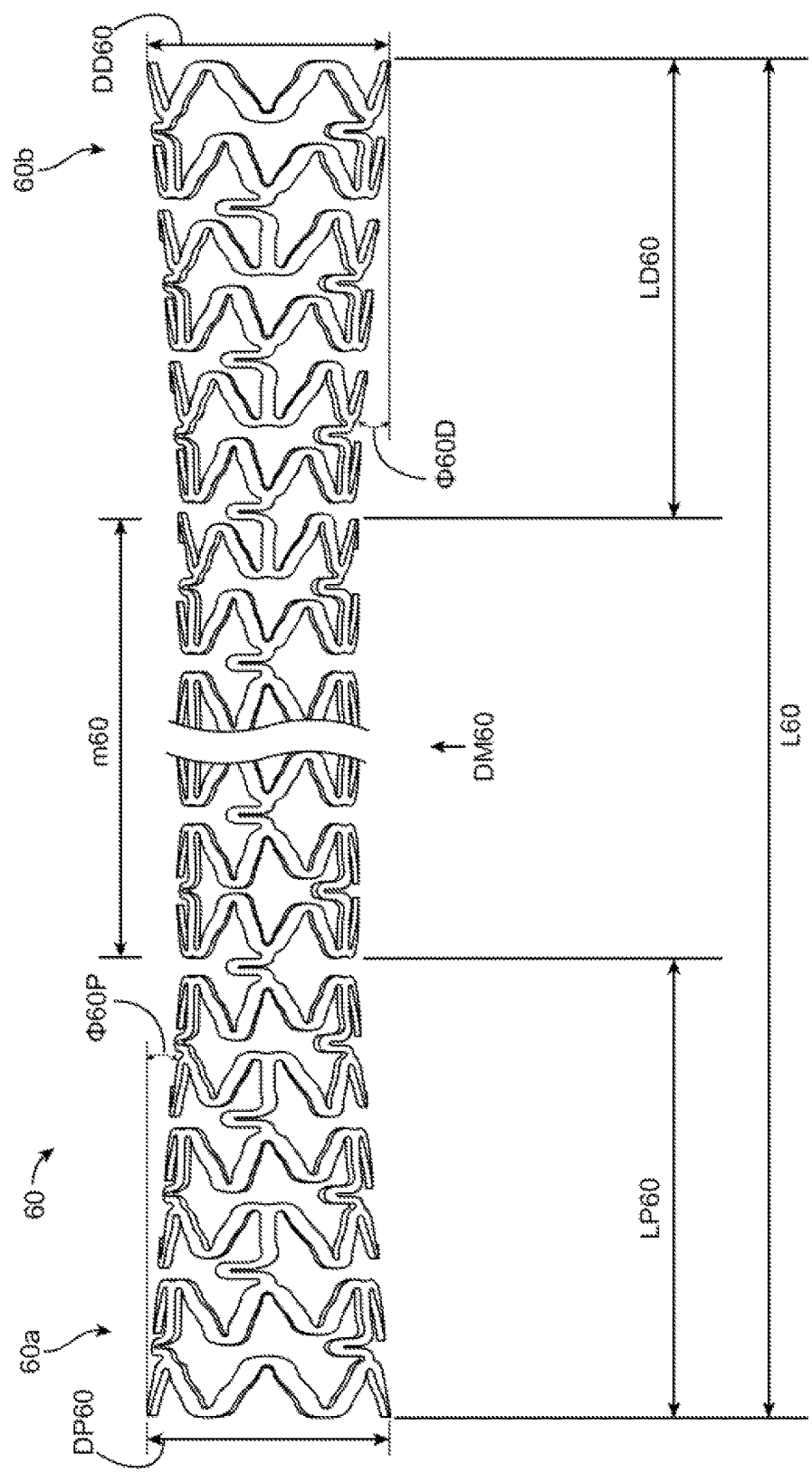
FIG. 5C is a side view of a tapered scaffold according to a third aspect of the disclosure.

Referring to FIGS. 5A through 5C there is described embodiments of tapered scaffolds according to a second aspect of the disclosure. FIG. 5A shows a flattened view of a scaffold 40 or scaffold 60, each of which have tapered ends (FIG. 5A depicts the scaffold in a similar view as the scaffold of FIG. 3). The scaffolds 40 and 60 are made from a bioresorbable material forming a network of rings interconnected by links. FIGS. 5B and 5C are side views (r-z plane) of the scaffolds 40 and 60, respectively (FIGS. 5B and 5C depict scaffolds in a similar view as the scaffold of FIG. 2).

The drawings of FIGS. 5B and 5C depict the taper of the scaffold 40 and scaffold 60, which are different from the taper shown in FIGS. 1-4 in that the taper is not monotonically increasing from one end to the other end. Rather, there is a first taper decreasing monotonically from each end towards a middle portion. This taper may be described as a constant curvature taper or a linear (or non-linear) taper from each end to a middle portion that takes a cylindrical shape or zero taper. Preferably the taper is linear.

Referring to FIG. 5B the scaffold 40 has a distal end diameter DD40 and proximal end diameter DP40. DD40 may be equal to, less than or greater than DP40. From these ends the diameter of the scaffold 40 decreases towards a middle portion diameter DM40. The change in diameter may be described approximately by a radius of curvature. Or, alternatively, the scaffold 40 may be described by two linear or non-linear tapers from the ends that meet at the middle portion (having diameter DM40) of the scaffold (these two taper types are defined above in connection with scaffold 20). The middle portion may be one, two or three rings with about equal diameters DM40 where the one ring or middle ring (of the three) is equidistant from the ends, closer to the proximal end 40a or closer to the distal end 40b. These rings of the middle portion thus have zero taper (or curvature) and have adjacent rings to the left and right (FIG. 5B) having equal (or non-equal) and opposite curvature or taper.

Using the same datum for FIG. 5B as that shown in FIG. 1 (i.e., origin for z axis is at proximal end), tangents of the diameter taper angles ϕ40P and ϕ40D are about (DM40−DD40)/LD40 and (DP40−DM40)/LP40, respectively, where LD40 is the distance from the end 40b to the middle portion M40, LP40 is the distance from the end 40a to the middle portion M40, and DM40 is the diameter of rings at the middle portion M40. Similarly, the tangents of width taper angles may be computed from the difference in widths between proximal end and middle portion, and distal end and middle portion widths of struts of rings.

In one example, the diameter taper angles ϕ40P and ϕ40D may have the following ranges and corresponding lengths LD40, LP40. ϕ40P may lie between about 0.5 to 10 degrees for LP of 0.5 to 5 mm. ϕ40D may lay between about 0.5 to 10 degrees for LD of 0.5 to 5 mm. The length of middle portion DM40 portion may correspond to a width of a ring. Over these same lengths the width of struts may lie between 50 microns and 100 microns.

Referring to FIG. 5C the scaffold 60 has a distal end diameter DD60 and proximal end diameter DP60. The scaffold 60 is similar to scaffold 40 except that in scaffold 60 the middle portion constitutes a substantial portion or a majority of the length of the scaffold 60. DD60 may be equal to, less than or greater than DP60. From these ends the diameter of the scaffold 60 decreases towards a middle portion diameter DM60. The scaffold 60 may be described by two linear or non-linear tapers from the ends that meet at the middle portion (having diameter DM60) of the scaffold (these taper types are defined above in connection with scaffold 20). The middle portion (M60) may be 30%, 40%, 50%, 60% or more of L60 with about equal diameters DM60 for all rings of the middle portion M60, and the middle portion M60 is equidistant from the ends, closer to the proximal end 60a or closer to the distal end 60b. These rings of the middle portion M60 thus describe a cylindrical portion of the scaffold 60 between the tapered ends.

Using the same datum for FIG. 5C as that shown in FIG. 1 (i.e., origin for z axis is at proximal end), taper angles ϕ60P and ϕ60D are about (DM60−DD60)/LD60 and (DP60−DM60)/LP60 where LD60 is the distance from the end 60b to the middle portion M60, LP60 is the distance from the end 60a to the middle portion M60, and DM60 is the diameter of rings at the middle portion M60. The taper angles ϕ60P ϕ60D may have the following ranges and corresponding lengths LD60, LP60. ϕ60P may lie between about 0.5 to 10 degrees for LP of 0.5 to 5 mm. ϕ60D may lay between about 0.5 to 10 degrees for LD of 0.5 to 5 mm. The length of middle portion M60 portion may correspond to one or a plurality of rings and links, and/or it may be about 2 mm, between about 2 to 5 mm or up to about 10 mm, or between about 10 mm and 20 mm. Over these same lengths of LP and LD the width of struts may lie between 50 microns and 100 microns.

Although the above definition of (diameter) taper in reference to scaffold 40 and 60 refer to a distal end diameter being greater than the proximal end, the terms "distal" and "proximal" should not be interpreted as meaning that the scaffold necessarily has its larger diameter end at a more distal end of a delivery catheter. The scaffold may be arranged on the catheter so that its proximal end has a larger diameter or smaller diameter than its distal end.

A mid-portion of either of the scaffolds 40 or 60 is shown in FIG. 5A. This view is similar to the view of FIG. 3. Thus, this view may be understood as a view one would see if the scaffold 40 or 60 were cut along its length, then unrolled and laid flat. Shown are taper angles ϕ1, ϕ2 which may be equal or non-equal in magnitude, and z axis from FIG. 1. A ring 44 includes struts 43 that are interconnected with each other at crowns 30a, 30b or 30c. A strut may have a rectangular cross-section characterized by an aspect ratio (AR), which is defined as the ratio of the width (ws) to the thickness (ts) (see FIGS. 4A, 4B) or AR for a strut is ws divided by ts. A link may have a rectangular cross-section characterized by an aspect ratio (AR), which is defined as the ratio of the width (wl) over thickness (tl), or the AR for a link is wl divided by tl (see FIG. 4B).

As in the case of scaffold 20, a ring 44 of scaffolds 40 or 60 may form a zig-zag or undulating pattern about the scaffold's bore axis A and have a tilt or taper corresponding to about the taper angle φ of the respective tapered part (see FIGS. 4A-4B for example). At the middle portion M40, M60 a ring has no taper. As indicated earlier, the tapers at proximal and distal ends may be the same or different. Moreover, the tapers may change from ring to ring. A scaffold 40, 60 having a non-constant taper among rings at the distal or proximal end is considered a non-linear taper. The ring 44 may alternatively have no tilt or taper, but instead have a slightly less, or greater outer diameter than its adjacent ring proximal or distal, respectively, so that over its length the scaffold also has the tapered shapes indicated in FIGS. 5B and 5C.

Struts 43 of a ring connect at either a U crown 30c, W crown 30a or Y crown 30b. A link 48a connects at one end to a Y crown 30b and at its opposite end to a W crown 30a. The scaffold 40, 60 may have two, three or four links 48 connecting adjacent rings at respective Y and W crowns. The number of crowns per ring at the middle portion may be 6, 7, 8, 9 or between 8 and 12. Referring to FIG. 5A there are four links 48 that connect ring 44a to ring 44b and four different links that connect ring 44b to ring 44c. There is no link that connects to a U crown 30c.

The scaffolds 40, 60 have ring, strut and link sizes that vary in dimension from the proximal ends 40a, 60a to the middle portions M40, M60 and from the distal ends 40b, 60b to the middle portions M40, M60. This may be readily seen by comparing the relative widths among rings 44d, 44e and 44f (distal end) and comparing the relative widths among rings 44a, 44b and 44c (proximal end). In some embodiments the link and/or ring sizes vary in a similar way as the outer diameter changes from proximal end to middle portion and from distal end to middle portion, although the disclosure contemplates other constructions as well in response to a clinical need (for example, there may be little to no change in width for struts or links, or only the struts change, or there is a change in width for only the proximal end section). The embodiment of scaffolds 40 and 60 depicted in FIG. 5A have both struts 43 and link 48 widths, e.g., ws and wl, that may vary in a similar way to the change in outer diameters along the z-axis. Thus, for struts nearest to end 40a, 60a the struts 43 have greater widths than struts further from end 40a, 60a of the proximal end portion of the scaffold 40 and 60, respectively. And struts nearest to end 40b, 60b the struts 43 have greater widths than struts further from end 40b, 60b of the distal end portion of the scaffolds 40 and 60, respectively. These same relationships may apply to the links connecting rings for scaffolds 40, 60.

According to some embodiments of the scaffold 40 or 60 a diameter, diameter width or link sizes may be chosen in accordance with EQS. 2A-2B.

$$Di = ((D2 - D1)/L) * zi + D1 \quad \text{EQ. 2A}$$
$$= \text{Tan}(\phi) * zi + D1$$

$$Wi = ((W2 - W1)/L) * zi + W1 \quad \text{EQ. 2B}$$
$$= \text{Tan}(\phi) * zi + W1$$

wherein,

D2−D1 is the difference in diameters, either between the middle portion and distal end 40b, 60b, or between the proximal end 40a, 60a and middle portion;

W2−W1 is the difference in width for a ring strut (or connecting link to the left or right of the ring strut), either between the middle portion and distal end 40b, 60b, or between the proximal end 40a, 60a and middle portion;

L is the respective lengths from the proximal end to middle portion or middle portion to distal end;

Zi is the distance in z from the proximal end to the midpoint of the ith ring or link, or the distance in z from the middle portion to the midpoint of the ith ring or link (zi L), the taper angle φ for either the proximal end portion or distal end portion may range from 0.5 to 10 Degrees, 5 and 15 degrees, more narrowly between 1 to 5 degrees, 4 to 6 degrees, 5-10 degrees, or more narrowly between 5-8 degrees (these ranges will be appreciated in view of the scope of contemplated clinical needs addressed by the invention); and W1 is the width of a strut (or a link) for the first ring at the proximal end or distal end, respectively.

Figure 6A:
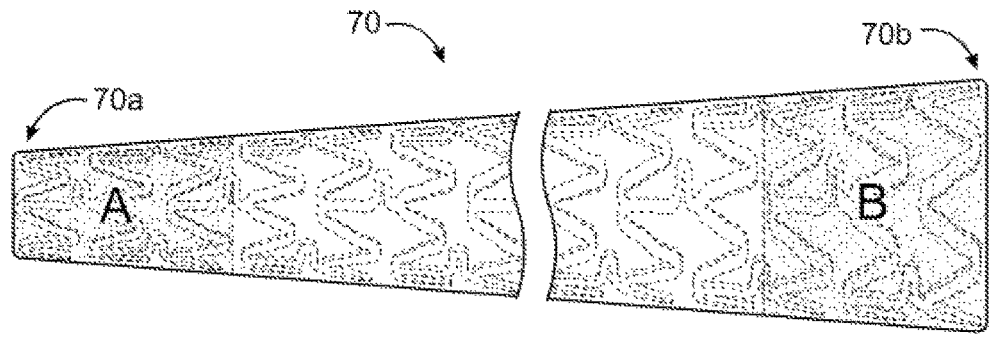
FIGS. 6A, 6B, and 6C are side views of the frustum and scaffolds of FIGS. 2, 5B and 5C, respectively, encased in a form-fitting sheath according to a fourth aspect of the disclosure.
Figure 6B:
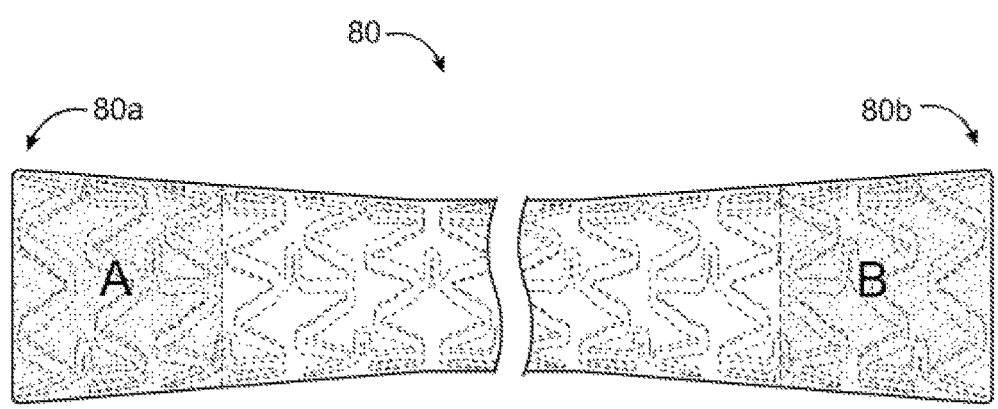
Figure 6C:
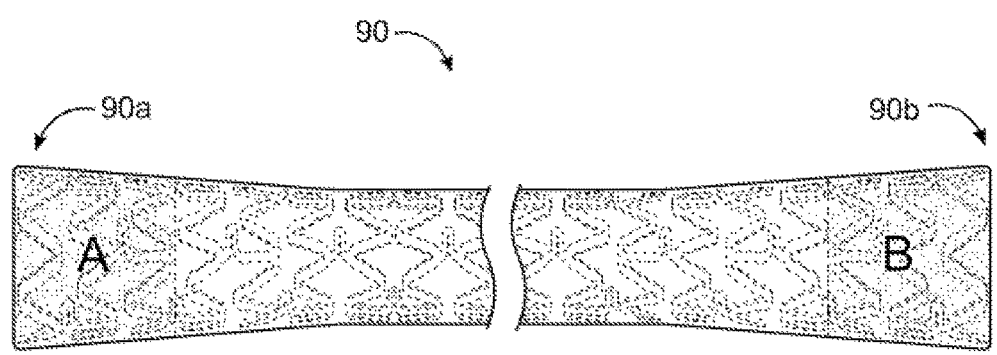

According to another aspect of the disclosure there is disclosed a stent-graft and scaffold-graft, the former comprising a durable polymer and the later comprising a bioresorbable polymer. Examples of these devices are shown in FIGS. 6A, 6B and 6C. The following description will refer to a scaffold-graft, with the understanding that the same description applies to a stent-graft with the exception of the material type(s) between stent/scaffold.

A first embodiment of a scaffold-graft of FIG. 6A includes the frustum 20 described previously in connection with FIGS. 1-4 encased or encapsulated within a porous sheath 70. The sheath 70 has a proximal end 70a and distal end 70b that matches with the distal and proximal ends 20a, 20b of the frustum 20. The sheath or jacket 70 may be made from a durable or bioresorbable polymer. The jacket 70 conforms to the same dimensions as the scaffold 20, as shown.

A second embodiment scaffold-graft of FIG. 6B includes the frustum 40 described previously in connection with FIGS. 1-4 encased or encapsulated within a porous sheath 80. The sheath 80 has a proximal end 80a and distal end 80b that matches with the distal and proximal ends 40a, 40b of the frustum 40. The sheath or jacket 80 may be made form a durable or bioresorbable polymer. The jacket 80 conforms to the same dimensions as the scaffold 40, as shown.

A third embodiment scaffold-graft of FIG. 6C includes the frustum 60 described previously in connection with FIGS. 1-4 encased or encapsulated within in a porous sheath 90. The sheath 90 has a proximal end 90a and distal end 90b that matches with the distal and proximal ends 60a, 60b of the frustum 60. The sheath or jacket 90 may be made form a durable or bioresorbable polymer. The jacket 90 conforms to the same dimensions as the scaffold 60, as shown.

As indicated in the drawings, the first, second and third embodiments of the scaffold-grafts have a section labeled "A" and a section labeled "B", which refer to an outer surface or abluminal side surface area over the length indicated (by the dashed lines) of the sheath nearest the respective ends, e.g., end 70a and 70b. These surface areas of the sheath have a higher porosity than the surface area of the sheath portion between A and B.

TABLE 1 discloses various properties of scaffolds according to another aspect of the disclosure. For example, the TABLE 1 properties may be adopted for any of the scaffolds 20, 40, 60 and 70-90. The additive manufacturing (AM) methods referred to in TABLE 1 are Selective Laser Sintering (SLS), Fused Deposition modeling (FDM), and Stereolithography (SLA).

TABLE 1

| Parameter | Range | AM Process | Comment | Material choice |
|---|---|---|---|---|
| Outer diameter, $D(z)$ | 2 mm-10 mm | SLA, FDM, SLS | 'z' dependence can be linear monotonic function or non-linear function. E.g. "D (z)" can be linear tapering or non-linear such as flared end with curved middle. | Durable polymer choice: PTFE, PVDF, segmented PU, PET, PVS, EVAL, PMMA-co-HEMA, |
| Width of strut or link, $W(z)$ | 25 um-500 um | SLA, FDM, SLS | | |
| Thickness of strut or link, $t(z)$ | 10 um-500 um | SLA, FDM, SLS | | |
| Maximum circular unsupported surface area MCUSA(z) | 0.4-1.75 mm² | SLA, FDM, SLS | $MCUSA_{scaff}(z)$ is a function of w, # links/ring, # ring/mm, surface area of link/nominal link length $MCA_{scaff}(z)$ applies for a scaffold pattern. However embodiment is possible to make graft-like porous scaffold, in which case links and rings are porous hence $P_{graft}(z)$ applies and $MCA_{scaff}(z)$ applies to the overall geometry. | Absorbable polymer choice: PLLA, PLGA, PLLA-co-PCL, PHB, PHBV, PGS Aqueous Swellability blend component choice: PEO, PVP, PEO-PLLA |
| Modulus of elasticity, $E_{int}(r, z)$ | 0.5-12 GPa | SLA, FDM, SLS | $E_{int}(r, z)$ depends on selection of polymer backbone, polymer MW, and polymer composition. Also depends on process condition affecting chain dynamics, state of polymer phase such as % crystallinity, degree of orientation, X-link density. | |
| Elongation before break | 0.4%-700% | | This is an intrinsic material property, a measure of polymer toughness, viscous damping potential, ductile mode of failure potential. | |
| Aqueous Swellability $m(z)$ | 0.05% (non-swellable)-50% (hydrogel property) | SLA, FDM, SLS | This may be applicable in AV graft application and PVD application, where compliance matching at anastomoses is needed for better clinical outcome. Also for AV graft a swellable anastomosis connection may prevent chronic trauma and cellular hyperplasia on the venous side. | |
| $P_{graft}(z)$ | Pore size 20 um-150 um | SLA, FDM, SLS, braiding | $P_{graft}(z)$ applies for a graft or a covering over a scaffold. | |

In some embodiments a tapered scaffold is intended for treating lesions in coronary vasculature. According to these embodiments a tapered scaffold, e.g., scaffold 20, may be used to treat vasculatures having a tapered lumen, or narrowed portions. For these embodiments TABLE 2 lists examples of proximal and distal end diameters, lengths and Tan (0) values for coronary scaffolds. Rows 1-3 in TABLE 2 list properties for an embodiment of a Right Coronary Artery, Left Anterior Descending Artery, and Left Circumflex Artery frustum scaffold. For the embodiments described in rows 1-3 a strut width for a ring at a proximal end is about 50 microns at a proximal end and at a distal end about 100 microns for a bioresorbable polymer, about 100 microns at a proximal end and at a distal end about 200 microns for a bioresorbable polymer, or at a proximal end about 80 microns and about 220 microns at a distal end.

TABLE 2

Frustum Scaffold for Coronary Applications

| | Right Coronary Artery | Left Anterior Descending Artery | Left Circumflex Artery |
|---|---|---|---|
| Proximal diameter | 3.4 mm | 3.1 mm | 2.8 mm |
| Distal diameter | 2.9 mm | 1.7 mm | 1.9 mm |
| Length | 55 mm | 74 mm | 35 mm |
| Tangent of diameter taper angle | 0.009 | 0.019 | 0.026 |
| Tangent of strut width taper angle | 0.009 | 0.019 | 0.026 |
| Range of proximal diameters | 3.4-4.7 mm | 3.1-5.1 mm | 2.8-4.0 mm |
| Range of distal diameters | 1.9-2.9 mm | 1.4-2.1 mm | 1.3-1.9 mm |

TABLE 2-continued

Frustum Scaffold for Coronary Applications

|  | Right Coronary Artery | Left Anterior Descending Artery | Left Circumflex Artery |
|---|---|---|---|
| Range of lengths | 55-86 mm | 74-100 mm | 35-56 mm |
| Strut width range at distal end | 200-240 μm | 200-240 μm | 200-240 μm |
| Strut width range at proximal end | 80-120 μm | 40-70 μm | 20-50 μm |

The tangent of taper angles for strut widths may apply to the embodiments of rows 1-3 or the additional embodiments of the frustum scaffold in rows 6-8 of TABLE 2.

Figure 7:
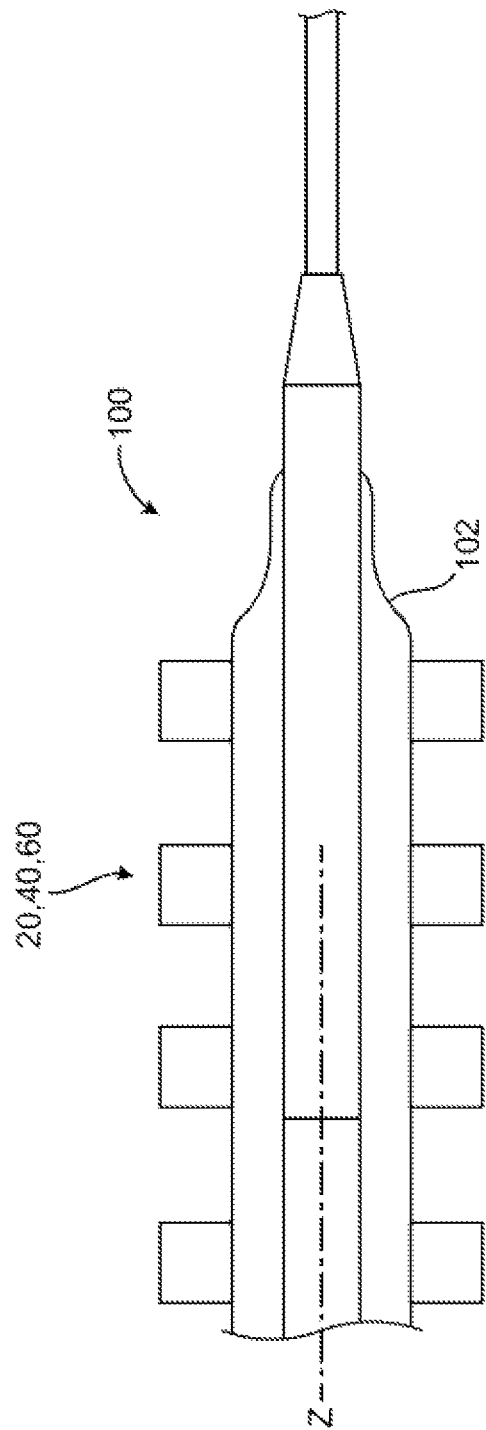
FIG. 7 shows a side view of a scaffold crimped to a balloon of a balloon catheter. The scaffold corresponds to any of the scaffolds according to the first, second, third or fourth aspects of the disclosure.

Referring to FIG. 7 there is shown a scaffold crimped to a balloon 102 of a balloon catheter 100. The scaffold may correspond to any of scaffolds 20, 40, or 60. The scaffold may or may not be contained within a sheath. The scaffold is expanded on a tapered, frustum-shaped or flared balloon 102 conforming to the respective shapes of the scaffold 20, 40 or 60. The scaffolds are plastically deformed by the balloon. The scaffold is crimped to the balloon by a crimping process. The crimping process may be performed by using angled blades within a crimping head, or by modifying an existing crimping head so that the blades form a tapered shape within the iris conforming to the tapered body.

According to a first method for crimping a tapered scaffold to a balloon may use an iris-type crimping mechanism having a plurality of blades that impart a radial compressive force on the scaffold. Tapered crimping stages for the crimping mechanism may be set across the length of the crimper, by adjusting crimper activation arms such that one closes to a smaller diameter than the other.

According to a second method for crimping uses an iris-type crimper with tapered segments/dies/blades. When brought down on the scaffold surface the angled blades form a tapered shape, which can be adjusted to accommodate a range of tapers.

According to a third method for crimping a frustum scaffold there is a preformed sheath with a constant OD and a tapered ID. The sheath is disposed between crimper blades and a surface of the scaffold. Effectively the sheath wall thickness changes along its length to provide a varying compression to match the frustum shaped, or tapered scaffold. Thus, a sheath having a thick end disposed over the frustum end having the smaller diameter, and the sheath becoming thinner towards the end with the higher diameter. Thus, when the crimper blades, e.g., straight or angled, bear down on sheath the tapered scaffold may be crimped to an about cylindrical shape where the reduction in the higher end diameter from crimping defines the crossing profile of the scaffold.

Example A

Arteriovenous fistulae are becoming a primary method of vascular access for hemodialysis patients. Still, failure rate is high often due to non-maturation of fistula due to complex hemodynamic factors within vessels. By implanting a prosthesis that is capable of functioning as a coupler between the artery and vein, one can better control the velocity profile within/between the vessels, thereby reducing areas of low/oscillatory shear stress, minimizing neointimal growth, and reducing the prevalence of stenosis within the fistulae space.

According to one embodiment, the scaffold 20 is used as an intravascular support for supporting a venous portion of an arteriovenous fistula (AVF). According to this application the proximal end 20a would be located nearest the fistula and the distal end 20b would be located furthest the fistula. As the vein matures the size increases. The taper angle for the frustum scaffold may vary from about 5 to 8 degrees up to 10 to 12 degrees. Generally speaking DD may be from 2 to 3, or up to about six times larger than DP. A frustum scaffold 2 is made from poly(L-lactide) (PLLA) using fused deposition modeling (FDM). The molecular weight of PLLA can range from 10-600 kDa. The temperature of the heated nozzle can be adjusted from 70-220 Degrees Celsius. The PLLA filament can be constructed by heating under tensile strain to introduce orientation in the filaments before they are fed from the "build material" spool into the FDM machine nozzle. With reference to FIG. 2, the scaffold 20 dimensions are DP=9 mm, DD=6 mm and L=36 mm and the taper angle is 8 degrees. The wall thickness is constant throughout and equal to about 360 microns. A strut width is 200 microns at the proximal end and 800 microns at the distal end.

According to other examples of a scaffold for AV fistula, there are the properties provided in TABLE A.

TABLE A

Embodiment 1:
Frustum scaffold having linear tapered,
made from an absorbable or durable polymer.
Properties:

Thickness range, t = 75-200 um, constant wall thickness for struts and links.
Scaffold Length range, L = 50-100 mm
Proximal diameter range, DD = 7-12 mm proximal diameter
Distal diameter range, DP = 3-7 mm proximal diameter
Strut width w(between 0 to L) range, changing linearly from 50-450 microns (Proximal strut width range) to 25-250 microns (Distal strut width range)
MCUSA (dependent on strut and link width W) linearly decreasing, distal end range (0.75-1.25 mm$^2$) and proximal end range (0.4-0.75 mm$^2$)
Elasticity modulus is constant with a range of (0.5-3.5 GPa)
Aqueous Swellability is constant with a range of (0.01%-2.75%)
Above geometry will be made from absorbable PLLA blended with 95 PLLA-co- 5PCL (at blend ratio 97.5:2.5 w/w)
Above geometry will also be made from durable PVDF polymer blended with 85 PVDF-co- 15 HFP (at blend ratio 70:30 w/w)

In one particular example the scaffold may have the following properties:
Wall thickness is t=100 μm and about constant for all struts and links.
Scaffold Length is L=100 mm.
Distal diameter is 6 mm.
Proximal diameter is 3 mm.
The width of struts for rings over length L increases linearly from 100 microns (proximal end ring) to 200 microns (distal end ring)
MCUSA (see relevant variables affecting MCUSA in TABLE 1) linearly decreasing from distal end to proximal end with distal end being 0.6 mm$^2$ and proximal end being 0.4 mm$^2$.
Elasticity modulus is constant with a range of 3-3.5 GPa
Aqueous Swellability is constant with a range of about 0.02% (non swellable)
Above geometry is made from absorbable PLLA blended with 95 PLLA-co-5PCL (at blend ratio 97.5:2.5 w/w) by fused deposition modeling (FDM).

Above geometry is alternatively made from a durable Polyethylene terephthalate (PET) by fused deposition modeling (FDM).

Above geometry is alternatively made from a durable Photocurable Polyurethane polymer using stereolithography (SLA)

In further embodiments, the scaffold for AV fistula may be viewed as assisting with coupling the vein to artery in such a manner as to enhance maturation rate of the vein and maintain event-free venous outflow access for dialysis patients. By utilizing a 3-D printing or additive manufacturing technique method, a coupling medical device (or coupler) can be made with region-selective spatial distribution of both or one of mechanical and biological interaction properties. These region-selective properties, made possible by additive manufacturing techniques disclosed herein, should in some instances provide a more effective coupler for a fistula than a more traditional subtraction-type manufacturing technique (such as cutting a stent from a tube). An implant for an AV fistula may be regarded as a coupler having mechanical design features tailored for promoting the desired vein maturation. The coupler is made using a 3-D fabrication process. This 3-D design may be tailored in both the polar (r, θ) and Z (axial) direction. The type of design features contemplated include items (a) and (b):

a) Spatial distribution of one or more mechanical properties in a 3-D structure by way of a combination of material for select regions of a unitary 3-D structure.
  i. Examples of material types are composites of metal-polymer; ceramic-polymer; metal-ceramic-polymer created by binder jetting, material extrusion, and/or material jetting.
  ii. Size of Nanoparticle, extruded filament properties, and thermo-mechanical properties of materials are key metrics for material properties.
  iii. A spatial distribution or change in material may be created to dial in a mechanical property for matching compliance and/or to conform to the implant site. For example, to minimize a compliance mismatch at the junction of tissue and the coupler, such as blood vessel unsupported walls and edge of a coupler, coupler material near the proximal and/or distal edge of the coupler is chosen to cause a decrease in the radial stiffness so that the radial stiffness more closely matches the adjacent vessel walls.
  iv. Material is altered in a local region to increase toughness (e.g., a crown of a ring element) or radial stiffness is increased locally by a composite material (as opposed to dimensions of, e.g., a strut width or thickness).
  v. Redundant crests: a lower Tg or faster degrading material forms a portion of load bearing structure, while other parts are made from lower degrading or non-degrading material, such as at the crown of a ring. As the lower Tg or faster degrading material begins to breakdown and its contribution to strength/stiffness becomes minimal, a stiffness property of the scaffold is lowered.

b) Spatial distribution of implant geometry. The coupler geometry, e.g., cross-sectional inertia or area (A) in the (r, θ) bending plane varies as a function of axial position of the coupler, i.e. A=A(z). Variations in geometry may include one or more of the following:
  i. A $(z)=A_o$=constant for $0<z<z_o$; A $(z)=A_o+A(z)$ for $z_o<z$; i.e. the cross-sectional geometry affecting mechanical properties A(z) are essentially constant through zo, then vary. In some embodiments A(z) is a monotonically decreasing linear function of z. As such, the coupler has geometry that results in a gradual decrease in an outer diameter or strut thickness. With regard to the decrease in diameter, placement of the narrowest diameter close to the anastomosis can help create a smooth curvature at the anastomosis rather than a steep take-off angle.
  ii. A(z) has a minimum value at a location between a proximal and distal end of the coupler. A mechanical property such as diameter or strut thickness decreases then increases as a function of z, such as in the embodiments disclosed herein.
  iii. A coupler cross-sectional axis of symmetry not parallel to the Z axis. For example, the coupler is a tubular body that is curved. Near the proximal end there is a curve, such that the coupler naturally forces the vein to take an optimal angle with respect to artery for a better clinical outcome.
  iv. Ao is made so that there is a 5-75% oversized compared to a vein diameter. The coupler is an intravascular support that introduces a stretch on the vein at the time of implantation. This corresponds to a vein location more distal of the anastomosis where increased vascular pressure from the artery causes the vein lumen to expand when matured.
  v. A coupler geometry, e.g., arrangement of rings interconnected by links, is patterned as a function of z to increase a stiffness in bending, radial or crush, such as where material stress-strain properties, e.g., young's modulus or fracture toughness, are adversely affected locally as a byproduct of designing for a particular biological outcome (faster degradation or tissue in-growth).

According to the embodiments, changes in geometry or A(z) are desirable when the coupler is designed to have a surface texture or porosity, throughout or only for a portion thereof to promote tissue ingrowth resulting in a variance in stress-strain or degradation properties in the coupler. Changes in stress-strain behavior or degradation can be compensated by changes in geometry using additive manufacturing. Other changes affecting mechanical properties include material selection variations over the coupler affecting mechanical properties include changes to modulus E, glass and meting temperatures (Tg and Tm, respectively), and the percentage crystallinity affecting strength/stiffness and toughness properties. In accordance with the disclosure 3-D printing or additive manufacturing is used to compensate in terms of geometry to affect the mechanical property.

Example B

This embodiment pertains to the scaffolds 40 or 60 (see FIGS. 5A-5C). According to this example, the scaffold when implanted can exhibit low mechanical trauma; hence, it can reduce if not eliminate any hyperplastic cellular response. Hyperplastic cellular response is known to cause soft-tissue stenosis or obstruction.

Referring to TABLE B, below, the overall size, i.e., diameter ranges and lengths, accommodates the various diameters encountered for longer vasculature that taper with length. These geometries are far more practical utilizing AM methods and in several of the embodiments outlined below it will be understood that traditional manufacturing methods for scaffold made from a tube cannot be used, or are simply impractical and of little value or utility in achieving stated the above-stated goals for tapered scaffolds.

TABLE B

Embodiment 2:
Flared End polymeric scaffold, absorbed or durable polymer.
Properties:

Thickness range, t = 75-150 μm and constant for all struts and links
Scaffold Length range, L = 50-100 mm length
Distal end (DD40, DD60) diameter range is 2-5 mm or 3-8 mm
Proximal end (DP40, DP60) diameter range is 2-5 mm or 3-8 mm
Middle section diameter range (DM40, DM60) = 3-5 mm.
Strut width w(between 0 to L) range, changing linearly from 50-450 microns (distal strut width range) to 25-250 microns (proximal strut width range)
MCUSA dependent on, and defined by strut and link width linearly decreasing distal range (0.75-1.25 mm$^2$) proximal range (0.4-0.75 mm$^2$)
Elasticity modulus at distal end (2-5 mm from end) constant at a value range of (0.5-1.5 GPa), at proximal end (2-5 mm from end) constant at a value range of (0.5-1.5 GPa) and linearly varying at the middle section (M40, M60) with range of (1-3.5 GPa). At ends material is PLLA-co-PCL blended with PEO or PVP. In middle portion material is PLLA-co-PCL.
Aqueous Swellability at distal end (2-5 mm from end) constant at a value range of (5-20% w/w), at proximal end (2-5 mm from end) constant at a value range of (5-20% w/w); and constant for middle portion (M40, M60) with a range of (0.05%-2.5%)
Above geometry will be made from absorbable PLLA blended with 95 PLLA-co- 5PCL (at blend ratio 97.5:2.5 w/w)
Above geometry may also be made from durable PVDF polymer blended with 85 PVDF-co- 15 PCL (at blend ratio 70:30 w/w)
Aqueous swellability at the ends will be obtained by blending hydrophilic polymers, e.g., those listed in TABLE 1 (blend ratio 5-20% w/w).

Example C

This embodiment pertains to scaffolds 70, 80 or 90. The scaffold is an AV graft for dialysis access. The ranges given in TABLE C reflect the expected range of vein and artery sizes. These geometries are far more practical utilizing AM methods and in several of the embodiments outlined below it will be understood that traditional manufacturing methods for scaffold made from a tube cannot be used, or are simply impractical and of little value or utility in achieving stated the above-stated goals for tapered scaffolds.

TABLE C

Embodiment 3:
Polymeric scaffold, Absorbable or durable, with a porous jacket
Properties:

Scaffold or stent properties the same as embodiments 1 or 2.
A durable or absorbable polymer jacket with axially varying porosity will be applied over the scaffold.
Jacket/sheath porosity P$_{graft}$(z) will be designed at distal 2-5 mm at a value range of (40-80 μm pore size) for Section B, proximal 2-5 mm at a value range of (40-80 μm pore size) for Section A; constant over rest of the axial section with a range of (15-30 μm pore size)

Example D

AM methods may also be used to fabricate scaffold with rapidly degrading links between rings. The links are designed to break or resorb away after an initial period which may be two weeks to one months, one to two months, three to four months, or later than four months. A scaffold can be designed with such rapidly degrading link structures that acutely or initially provide longitudinal stability and then separate through degradation or breaking due to degradation after the scaffold is encapsulated in tissue. This encapsulated scaffold, having no or less links, is more flexible and more closely matches the bending behavior of the vessel. The design is useful when crossed by other devices.

The links may be integral with the rings through use of AM methods for fabrication of the scaffold. A portion of or an entire link structure may be made of a material with a faster degradation property. As a bioabsorbable scaffold degrades, the strength of the faster degrading link structure or portion of the link structure weakens faster than the remainder of the scaffold and becomes susceptible to breaking. Adjacent rings may be connected by one or more fast degrading links. All the links connecting adjacent rings may be fast degrading links. Some or all of the rings may be connected by the fast degrading links.

The rapidly degrading structure such as redundant rings, crest features, and link structures may be made from may be made to have a faster degradation property than the rest of a scaffold in various ways. One way is that the structures may be made of the same material as the rest of the scaffold, but with a lower molecular weight. For example, the polymer of the redundant structures may be 50 to 70%, 70 to 80%, or 80 to 90% of the molecular weight of the polymer of the rest of the scaffold. Another way is that the redundant structures may be made of a different, faster degrading polymer than the remainder of the scaffold. For example, the remainder of the scaffold may be made PLLA and the redundant structure made be made of PDLLA or PLGA. Still another way is that the structures may be made of the same material as the rest of the scaffold, but with additives that increase the degradation rate. Such additives can include monomers such as L-lactide and glycolide and bioceramic particles such as calcium sulfate particles.

According to one embodiment of a tapered scaffold, there is a frangible link made with 85:15 PGA:PLLA w/w ratio and strut width of about 100 μm and thickness 25 μm. Or 75:25 PEG:PGA w/w ratio can be used for the same strut dimension.

Example E

1. Compliance Matching Stent/Scaffold, Vary Density of Material Across the Width, Same Material but Change Degradation Characteristics by Changing Density, Crystallinity Degree and Morphology of Crystals In further embodiments, a scaffold can be fabricated with a spatially varying compliance reduce the compliance mismatch between the scaffold and vessel through variation of the density across the width of the struts of the scaffold. In this way, the scaffold can be made of the same material throughout with a spatially varying compliance.

2. Compliance Matching Stents that have Lower Material Density in Proximal and Distal Ends When a scaffold is implanted in a vessel segment, the compliance in the axial direction undergoes and discontinuous change at the proximal and distal ends from the scaffold compliance (low) to the native vessel (high). This discontinuity in compliance is generally undesirable and can cause problems.

AM methods can be used to fabricated scaffolds which decrease the compliance mismatch at the ends of the scaffold. A scaffold can be made with reduced the material density at the ends of the scaffold which will increase the compliance of the stent in the areas of low material density. The compliance of the ends of the stents can tailor so that they match or more closely match the compliance of the native vessel. The material density of the scaffold in the end sections at the distal end and proximal end may be reduced. All or some of the struts can have reduced material density as compared to the middle axial section of the scaffold. For example, portions with reduced density can include crest regions, links, or both crest regions and links. The end section may include one, two, or three rings at the ends of the scaffold.

Embodiments 1 and 2 described above are examples of tapered scaffolds having compliance-matched ends.

3. In the Case of Degradable Scaffolds, Tailoring Porosity to Control Degradation AM methods may further be used control or obtain selected degradation behavior of a bioabsorbable scaffold by tailoring the porosity in selected portions of a scaffold to control the way the scaffold degrades. The degradation rate of selected portion increases/decreases as the porosity increases/decreases. A scaffold can be made with AM methods having selected portions with higher or lower porosity than other portions of the scaffold.

For instance, a greater porosity can be incorporated in links to facilitate faster degradation at these locations. This behavior results in faster decoupling of the scaffold rings form one another which is particularly important in vessels such as the superficial femoral artery that are subjected to significant axial and torsional forces.

In addition, the porosity of crest regions of a scaffold can be varied to control the time dependence of radial strength. Thus, the radial strength temporal profile can be controlled by varying the porosity of the crest regions. For example, the porosity the crest regions can be greater than the remainder of the scaffold to result in a faster decrease in radial strength. Alternatively, the crest regions may be nonporous or have a lower porosity of the remainder of the scaffold to allow the scaffold support a lumen for a requisite time period while allowing the remainder of the scaffold to degrade away faster.

Embodiments 1 and 2 described above are examples of tapered scaffolds having compliance-matched ends.

Additive Manufacturing Processes

The term "additive manufacturing" refers to technologies that create objects through joining of material to make objects from 3D model data. The term "3D printing" is often used synonymously with AM. Objects are created by sequential addition of material such as by sequential layering. The material may be in the form of a liquid, powder, solution, suspension, paper, or sheet material. Materials may include polymer, metals, ceramics or any combination thereof. Exemplary AM method include, but are not limited to, vat photopolymerization, stereolithography, material jetting, binder jetting, material extrusion, powder bed fusion, sheet Lamination, and directed energy deposition.

Fabricating implants from AM methods may be distinguished from traditional "subtractive" fabrication methods. In such traditional methods, a construct is fabricated by a conventional process followed by removal of material from the construct to form the implant. It may be either extremely difficult or impossible to fabricate the implant directly with the conventional process. Such processes include extrusion and injection molding. For example, a stent or scaffold may be formed from an extruded tube by laser cutting a pattern in the tube.

The various embodiments of the invention include creating a 3D model of an implant. The implant may be designed on a computer systems based on structure for treating a diseased anatomical structure. The 3D model may be based on imaging data of a patient. The implant may then be fabricated using an AM method based on the 3D model. In some embodiments, the entire feature of the implant is made from the AM method. In other embodiments, only a portion of an implant may be made by an AM method. In such cases, the AM method is used to add features or structure to an existing construct or implant structure made not necessarily made based on the 3D model. For example, an AM method may be used to add features based on a 3D model to a scaffold made by laser cutting a tube formed by extrusion. A significant advantage of AM methods over conventional manufacturing methods is the degree of flexibility in manufacturing structures with a desired shape, size, material, properties, and spatial variation of material and properties relatively quickly and inexpensively.

"Vat Photopolymerization" refers to an AM process in which liquid photopolymer in a vat is selectively cured by light-activated polymerization. "Stereolithography is an example of this process which employs a vat of liquid ultraviolet curable photopolymer "resin" and an ultraviolet laser to build parts' layers one at a time. For each layer, the laser beam traces a cross-section of the part pattern on the surface of the liquid resin. Exposure to the ultraviolet laser light cures and solidifies the pattern traced on the resin and joins it to the layer below.

"Material Jetting" refers to an AM process in which droplets of build material are selectively deposited. PolyJet™ from Solid Concepts of Los Angeles, Calif. is an example of this process.

"Binder Jetting" is an AM process in which a liquid bonding agent is selectively deposited to join powder materials. The ZPrinter line from 3DSYSTEMS of Rock Hill, S.C. uses this process.

"Material Extrusion" refers to an additive manufacturing process in which material is selectively dispensed through a nozzle or orifice. Stratasys' previously mentioned FDM technology is an example of this process.

"Fused Deposition Modeling (FDM)" is a solid-based rapid prototyping method that extrudes material, layer-by-layer, to build a model from 3D CAD data. The basic elements of an FDM system are a build platform, extrusion nozzle, and control system. Material is supplied in the form of filaments, which is fed into the extruder that will heat the material and each layer will fuse with the previous one. The extruder moves in the x-y plane to builds layer-by-layer the Z dimension.

"Powder Bed Fusion" is an AM process in which thermal energy selectively fuses regions of a powder bed. EOS direct metal laser sintering from 3DPARTS Manufacturing LLC in Indianapolis, Ind. is an example of this process.

"Sheet Lamination" is an AM process in which sheets of material are bonded to form an object. The Mcor Technologies of San Diego, Calif. printers use this type of process.

"Directed Energy Deposition" is an AM process in which focused thermal energy is used to fuse materials by melting as they are being deposited. The Optomec LENS systems of Albuquerque, N. Mex. are an example of this process.

Materials

The medical devices disclosed herein may be made partially or completely from a biodegradable, bioabsorbable, or biostable materials. The AM methods disclosed may use these materials to fabricate such medical devices. Biostable refers to materials that are not biodegradable. The terms biodegradable, bioabsorbable, and bioerodable are used interchangeably and refer to materials that are capable of being completely degraded and/or eroded when exposed to bodily fluids such as blood and can be gradually resorbed, absorbed, and/or eliminated by the body.

The materials that may be used in the AM methods for making medical devices include bioresorbable polymer, bioerodible metals, and biodegradable bioceramics. The medical devices can be made partially or completely of any combination of the materials disclosed herein A polymer for use in fabricating the medical devices can be biostable, bioabsorbable, biodegradable or bioerodable. The processes of breaking down and absorption of the polymer can be caused by, for example, hydrolysis and metabolic processes. The polymers may also be biosoluble or water soluble polymers. A biosoluble polymer corresponds to a polymer that is capable of dissolving in water in addition to, or even in the absence of hydrolysis and metabolic processes.

The medical devices may include partially or completely of bioresorbable polymers including poly(L-lactide) (PLLA), poly(D-lactide) (PDLA), polyglycolide (PGA), poly(D,L-lactide) (PDLLA), and poly(L-lactide-co-glycolide) (PLGA). The PLGA include those having a mole % of (LA:GA) of 85:15 (or a range of 82:18 to 88:12), 95:5 (or a range of 93:7 to 97:3), or commercially available PLGA products identified being 85:15 or 95:5 PLGA. Additional bioresorbable polymers include but are not limited to polyhydroxyalkanoates (PHA), poly(4-hydroxybutyrate) (P4HB), poly(caprolactone), (PCL) poly(trimethylene carbonate) (PTMC), poly(butylene succinate) (PBS), poly(p-dioxanone) (PDO), poly(ester amides) (PEA), and including copolymers (block, random, alternating) and blends of any combination of polymers disclosed.

Exemplary biosoluble or water soluble polymers include poly(vinyl alcohol) (PVA) and poly(ethylene glycol) (PEG). Water soluble polymers tend to absorb faster than a non-water soluble hydrolytically degradable polymer.

The medical devices may be formed partially or completely from hydrogels which are a physical or chemically crosslinked network of polymer that is capable of swelling due to absorption of a large volume of water in relation to the weight of the polymer. The crosslinks in the network can be covalent, electrostatic, hydrophobic, or dipole-dipole in character. The ability to swell is facilitated by the hydrophilicity of the polymer. Hydrophilic water-solubilizing groups that can be present include —OH, —COOH, —CONH$_2$, and CONH. Hydrogels can be formed from crosslinked water soluble polymers such as PEG or PVA. Hydrogels can also include crosslinked polymers that degrade by hydrolysis such as aliphatic polyesters.

The medical devices may include bioerodible metals or metal alloys including magnesium, iron, zinc, tungsten, and alloys including these metals. The metals may also include platinum, stainless steel, and nickel-titanium alloys.

Exemplary biodegradable ceramics include apatites and other calcium phosphates such as hydroxyapatite ($Ca_{10}(PO_4)_6(OH)_2$), floroapatite ($Ca_{10}(PO_4)_6F_2$), carbonate apatide ($Ca_{10}(PO_4)_6CO_3$), tricalcium phosphate ($Ca_3(PO_4)_2$), octacacium phosphate ($Ca_8H_2(PO_4)_65H2O$), octacalcium phosphate ($Ca_8H_2(PO_4)_6$-$5H_2O$), calcium pyrophosphate ($Ca_2P_2O_7$-$2H_2O$), dicalcium phosphate dehydrate ($CaHPO_4$-$2H_2O$). The term bioceramics also includes various bioactive glasses and glass ceramics derived from certain compositions in $SiO_2$—$Na_2O$—$K_2O$—$CaO$—$MgO$—$P_2O_5$ systems.

The bioabsorbable polymer portions of the devices may further include unreacted monomers or acids of bioabsorbable polymers including, but not limited to L-lactide, D-lactide, glycolide, caprolactone, L-lactic acid, D-lactic acid, glycolic acid, or caprolactic acid. A monomer content of a polymer composition can be 0.01 to 0.05 wt %, 0.05 to 0.1 wt %, 0.1 to 0.2 wt %, 0.2 to 0.3 wt %, 0.3 to 0.4 wt %, 0.4 to 0.5 wt %, 0.5 to 0.7 wt %, 0.7 to 1 wt %, or greater than 1 wt %. Any combination of polymer and monomer or acid with any concentration is disclosed.

All or part of the medical devices may be composites of at least two polymers, a metals and polymer, a ceramic and polymer, and ceramic and metal. The composites may include a matrix phase or region including a particulate phase dispersed throughout a matrix component. The matrix component is greater than 50 wt % or vol % and the particulate or minor component. Composites of a major/minor component include: polymer/polymer, polymer/metal, polymer/bioceramic, metal/polymer, and metal/bioceramic.

The composition of the minor component may be 0.01 to 0.1 wt % or vol %, 0.1 to 0.5 wt % or vol %, 0.5 to 1 wt % or vol %, 1 to 3 wt % or vol %, 3 to 5 wt % or vol %, 5 to 10 wt % or vol %, greater than 10 wt % or vol %. The particles may be spherical, roughly spherical, or fibers. The size of the particles may be 10 to 100 nm, 100 to 2,500 nm, 2,500 to 5000 nm, 5,000 to 10,000 nm, 10,000 to 100,000 microns, or greater than 100,000 nm. Particles in a range less than 10,000 may be referred to as nanoparticles.

Drug delivery particles may also be implantable devices as a part of a matrix component or independent of a matrix component. Drug delivery particles may include a delivery matrix and a therapeutic agent. The delivery matrix may be a composite or a polymer, metal, or ceramic. The particles include a matrix with the drug dispersed throughout the matrix material. Alternatively, the particle may have shell of polymer or metal with a drug within the shell. The size of the drug delivery particles may have the ranges described above.

Drugs

Therapeutic, active agents, or drugs, may be include in the scaffolds disclosed herein and include using AM methods. The drugs may include any agent which is a therapeutic, prophylactic, or a diagnostic agent, or any agent that is used to treat a disease or condition. Examples include, without limitation endothelial cell binding agent, anti-restenosis, pro- or anti-proliferative, chemotherapy agents, anti-inflammatory, blood thinners, antineoplastic, anti-thrombotic, antineoplastic, anti-infective, antibiotic, antimitotic, anti-platelet, anticoagulant, antifibrin, antithrombin, cytostatic, antibiotic, anti-enzymatic, anti-metabolic, angiogenic, cytoprotective, angiotensin converting enzyme (ACE) inhibiting, angiotensin II receptor antagonizing and/or cardioprotective active agents.

Active agents include, but are not limited to, heparin, paclitaxel, clobetasol, dexamethasone, novolimus, rapamycin (sirolimus), Biolimus A9 (Biosensors International, Singapore), deforolimus, AP23572 (Ariad Pharmaceuticals), tacrolimus, temsirolimus, pimecrolimus, novolimus, zotarolimus (ABT-578), 40-O-(2-hydroxyl)ethyl-rapamycin (everolimus), 40-O-(3-hydroxypropyl)rapamycin, 40-O-[2-(2-hydroxyl)ethoxy]ethyl-rapamycin, 40-O-tetrazolylrapamycin, and 40-epi-(N1-tetrazolyl)-rapamycin.

Active agents may be disposed on a surface of device or dispersed within all or a portion of a matrix component of a device.

The scaffolds may also include radiopaque agents to allow the device to be sufficiently radiopaque to be fluoroscopically visible under x-rays. Accurate scaffold placement is facilitated by real time visualization of the delivery of a scaffold. A cardiologist or interventional radiologist can track the delivery catheter through the patient's vasculature and precisely place the scaffold at the site of a lesion. This is typically accomplished by fluoroscopy or similar x-ray visualization procedures. For a scaffold to be fluoroscopically visible it must be more absorptive of x-rays than the surrounding tissue. Radiopaque materials in a scaffold may allow for its direct visualization.

Radiopaque Materials

Radiopaque materials can include, but are not limited to, contrast agents, biostable and erodible metals, metallic oxides, and biocompatible metallic salts. The radiopaque material may be dissolved or mixed as particles in a matrix component of the device. Representative iodinated contrast agents may include, but are not limited to, acetriozate, diatriozate, iodimide, ioglicate, iothalamate, ioxithalamate, selectan, uroselectan, diodone, metrizoate, metrizamide, iohexol, ioxaglate, iodixanol, lipidial, ethiodol, and combinations thereof. Representative examples of metals that may be used as radiopaque agents include, but are not limited to, iron, magnesium, zinc, platinum, gold, platinum, and tungsten. Additionally, oxides of such metals and other metals may be used as radiopaque agents. Representative biocompatible metallic salts include, but are not limited to, ferrous sulfate, ferrous gluconate, ferrous carbonate, ferrous chloride, ferrous fumarate, ferrous iodide, ferrous lactate, ferrous succinate, barium sulfate, bismuth subcarbonate, bismuth potassium tartrate, bismuth sodium iodide, bismuth sodium tartrate, bismuth sodium triglycollamate, bismuth subsalicylate, zinc acetate, zinc carbonate, zinc citrate, zinc iodate, zinc iodide, zinc lactate, zinc phosphate, zinc salicylate, zinc stearate, zinc sulfate, and combinations thereof. A dimension of the particles can be 10-100 μm, 100-200 μm, or greater than 200 μm.

Devices

As discussed above, scaffolds disclosed described herein may be used to address clinical needs in a number of areas including, but not limited to, coronary vascular disease, peripheral vascular disease, local oncology therapy, AV fistula implant, neurodegenerative disease, congestive heart failure, aneurysm, eliminating amputation, congenital heart disease, and plugging holes in arteries.

Among the embodiments contemplated, there is a self-expandable or self expanding tapered scaffold including a bioabsorbable polymer scaffold that elastically expands to the target diameter upon removal of an external constraint. The self expanding scaffold expands to a larger diameter when an external constraint is removed. This external constraint could be applied with a sheath that is oriented over a compressed scaffold. The sheath is applied to the scaffold after the scaffold has been compressed by a crimping process. After the stent is positioned at the implant site, the sheath may be retracted by a mechanism that is available at the end of the catheter system and is operable by the physician. The self expanding bioabsorbable scaffold property is achieved by imposing only elastic deformation to the scaffold during the manufacturing step that compresses the scaffold into the sheath.

The bioabsorbable scaffold, such as scaffold 40, 60 and 20 may be expanded by a balloon. In this embodiment the scaffold is plastically deformed during the manufacturing process to tightly compress the scaffold onto a balloon on a catheter system. The scaffold is deployed at the treatment site by inflation of the balloon which expands the scaffold. The balloon will induce areas of plastic stress in the bioabsorbable material to cause the scaffold to achieve and maintain the appropriate diameter on deployment. The scaffold is compressed onto a catheter by a crimping process.

Scaffolds according to some embodiments also address a need to maintain a low profile for struts exposed in the bloodstream, while ensuring the marker will be securely held in the strut. The concern addressed here is the degree thrombogenicity of the scaffold, which can be influenced by a strut thickness overall and/or protrusion from a strut surface. Blood compatibility, also known as hemocompatibility or thromboresistance, is a desired property for scaffolds and stents. The adverse event of scaffold thrombosis, while a very low frequency event, carries with it a high incidence of morbidity and mortality. To mitigate the risk of thrombosis, dual anti-platelet therapy is administered with all coronary scaffold and stent implantation. This is to reduce thrombus formation due to the procedure, vessel injury, and the implant itself. Scaffolds and stents are foreign bodies and they all have some degree of thrombogenicity. The thrombogenicity of a scaffold refers to its propensity to form thrombus and this is due to several factors, including strut thickness, strut width, strut shape, total scaffold surface area, scaffold pattern, scaffold length, scaffold diameter, surface roughness and surface chemistry. For scaffolds 20, 40, 60 the thickness of a strut and/or link may vary between about 80 to 150 microns, 80 to 120 microns, 80 to 110 microns, 80 to 100 microns, or the thickness may be about 100 microns, or the thickness may be up to 130 or 140 microns.

A scaffold according to the disclosure may have lengths of between 12 and 18 mm, 18 and 36 mm, 36 and 40 mm or even between 40 and 200 mm as fabricated or when implanted in an artery. Exemplary lengths include 12 mm, 14 mm, 18 mm, 24 mm, or 48 mm. The scaffold may have a pre-crimping or as-fabricated diameter of between 2-3 mm, 2.5-3.5 mm, 3-4 mm, 3-5 mm, 5-10 mm, 6-8 mm, or any value between and including these endpoints. Diameter may refer to the inner diameter or outer diameter of the scaffold. Exemplary diameters include 2.5 mm, 3.0 mm, 3.25 mm, 3.5 mm, 4 mm, 5 mm, or 6 mm.

Various embodiments include patient-specific, anatomy-matched implant devices created by AM methods. The anatomy-matched 3D models for making the implants are obtained from non-invasive imaging. Exemplary non-invasive imaging techniques including, but not limited to, magnetic resonance imaging (MRI), computed tomography (CT), and X-ray.

Exemplary implantable patient-specific implants include stents or scaffolds or implanting into a body lumen, stent-grants, shunts.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in claims should not be construed to limit the invention to the specific embodiments disclosed in the specification.

What is claimed is:
1. A medical device, comprising:
    a unitary network of rings interconnected by links and forming a scaffold, and the unitary network including a first flared end portion, a second flared end portion and a middle portion located between the flared end portions;

wherein a ring is formed by struts connected at crowns to form a zig-zag or undulating pattern of struts about a bore axis of the scaffold, wherein a link connects a ring to an adjacent ring at either a Y crown or a W crown, and wherein
an elasticity modulus for the rings interconnected by links of the flared end portions is constant and has a range of about 0.5 to 1.5 GPa, and the rings interconnected by links of the flared end portions consist of PLLA-co-PCL blended with PEO or PVP, and an elasticity modulus for the rings interconnected by links of the middle portion has a linearly varying elasticity modulus of 1.0 to 3.5 GPa, and the rings interconnected by links of the middle portion consist of PLLA-co-PCL.

2. The medical device of claim 1, wherein a width of the struts linearly varies from the first flared end portion to the middle portion, and wherein rings of the middle portion each have about the same diameter.

3. The medical device of claim 1, wherein a width of the links linearly varies from the first flared end portion to the middle portion.

4. The medical device of claim 1, wherein a taper at one or both of the first and second flared end portions is linear.

5. The medical device of claim 1, wherein the scaffold is encased in a sheath.

6. The medical device of claim 5, wherein the sheath has a higher porosity at a distal and/or proximal end than at a middle portion thereof.

7. The scaffold of claim 1, wherein an aqueous swellability at the first flared end portion is constant and has a range of 5-20% w/w, an aqueous swellability at the second flared end portion is constant at a range of 5-20% w/w, and an aqueous swellability is constant for the middle portion with a range of 0.05%-2.5%.

* * * * *